(12) United States Patent
Mousa

(10) Patent No.: US 9,480,703 B2
(45) Date of Patent: Nov. 1, 2016

(54) METHOD AND COMPOSITION OF GLYCOSAMINOGLYCANS IN SICKLE CELL AND VASCULAR DISORDERS

(71) Applicant: Shaker A. Mousa, Wynantskill, NY (US)

(72) Inventor: Shaker A. Mousa, Wynantskill, NY (US)

( * ) Notice: Subject to any disclaimer, the term of this patent is extended or adjusted under 35 U.S.C. 154(b) by 141 days.

(21) Appl. No.: 14/526,950

(22) Filed: Oct. 29, 2014

(65) Prior Publication Data

US 2015/0150818 A1 Jun. 4, 2015

Related U.S. Application Data

(60) Provisional application No. 61/896,876, filed on Oct. 29, 2013.

(51) Int. Cl.
| | |
|---|---|
| A61K 9/50 | (2006.01) |
| A61K 9/14 | (2006.01) |
| A61K 9/16 | (2006.01) |
| A61K 31/727 | (2006.01) |
| A61K 31/737 | (2006.01) |
| A61K 9/51 | (2006.01) |
| A61K 47/48 | (2006.01) |
| A61K 31/00 | (2006.01) |

(52) U.S. Cl.
CPC ........... *A61K 31/737* (2013.01); *A61K 9/5169* (2013.01); *A61K 31/00* (2013.01); *A61K 47/48923* (2013.01)

(58) Field of Classification Search
None
See application file for complete search history.

(56) References Cited

U.S. PATENT DOCUMENTS

| | | | | |
|---|---|---|---|---|
| 6,106,866 A | * | 8/2000 | Ranney | A61K 47/4823 424/489 |
| 2008/0220055 A1 | * | 9/2008 | Ludwig | A61K 47/488 424/450 |
| 2009/0074828 A1 | * | 3/2009 | Alexis | A61K 9/5123 424/422 |
| 2009/0186093 A1 | * | 7/2009 | Liu | A61K 9/5026 424/497 |
| 2011/0189299 A1 | * | 8/2011 | Okubo | A61K 9/0043 424/491 |
| 2015/0132399 A1 | * | 5/2015 | Mousa | A61K 31/727 424/501 |

OTHER PUBLICATIONS

Chakravarthi et al.; International Journal of Pharmaceutics 409(2011); pp. 111-120; available online Feb. 26, 2011.*
Phillips et al.; Anticancer Research 31: 411-420; 2011.*
Prokopiou et al.; Angiogenesis (2013) 16:503-524; available online Mar. 31, 2013.*
Sudha et al.; Clin. Exp. Metastasis (2012) 29:431-439; available online Mar. 14, 2012.*
Google Scholar NPL Search results; downloaded Jul. 21, 2016.*
SciFinder NPL search results #1; downloaded Jul. 21, 2016.*
SciFinder NPL search results #2; downloaded Jul. 21, 2016.*
SciFinder NPL search results #3; downloaded Jul. 21, 2016.*

* cited by examiner

*Primary Examiner* — Jeffrey T Palenik
(74) *Attorney, Agent, or Firm* — Schmeiser, Olsen & Watts, LLP; Jack P. Friedman

(57) ABSTRACT

A composition that includes a nanoparticle. The nanoparticle includes a shell which encapsulates sulfated non-anticoagulant heparin (SNACH). The shell includes poly L-arginine. The SNACH is ionically or covalently bonded to the poly L-arginine. A method for treating a disorder of a subject includes: administering to the subject a therapeutically effective amount of the composition for treating the disorder. The disorder is a vascular disorder, a complication of the vascular disorder, or a combination thereof.

20 Claims, 23 Drawing Sheets

Schematic diagram showing the synthesis of Chitosan-poly L-arginine conjugate.

L-Arginine Structure and Number of Arginine Repeating Units: x=10 -100 (poly-L-arginine, MW=2,000 -20,000 Da)

TFPI Calibration Curve

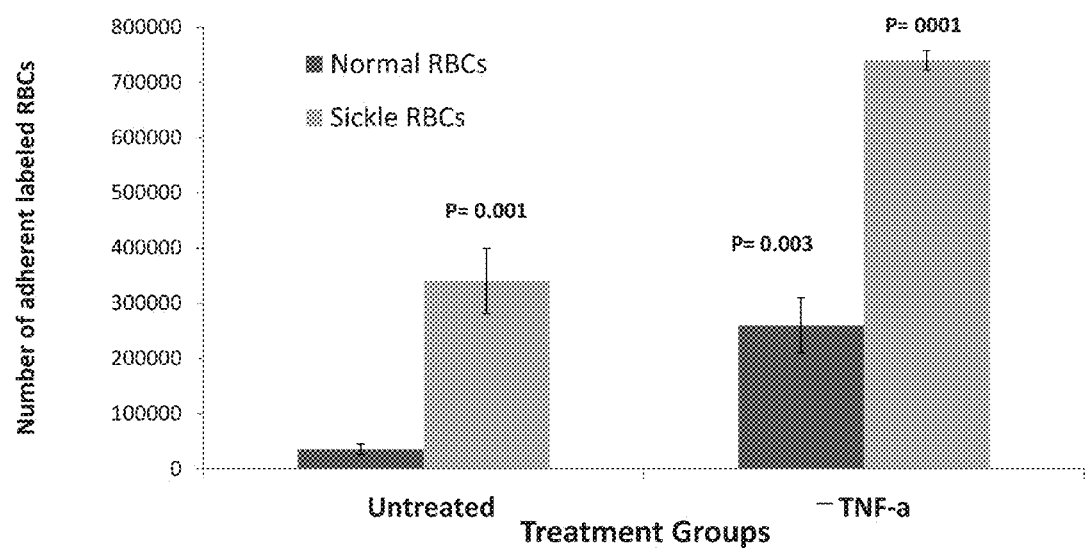
Figure 4: Adherence of normal and sickle RBCs adhesion to ECs with or without TNF-α treatment.

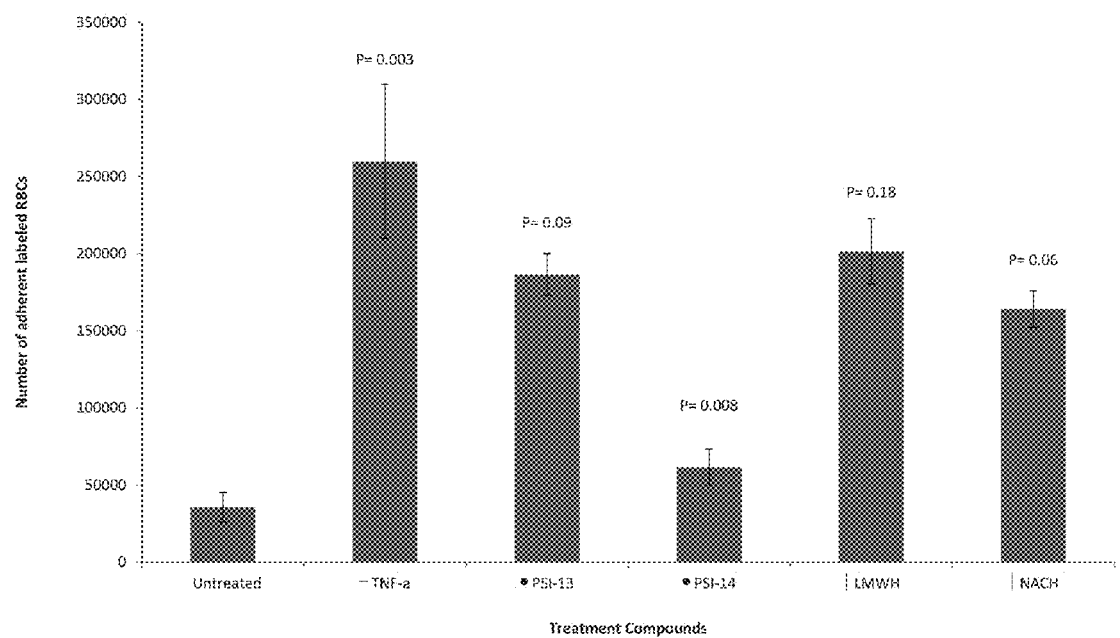
Figure 5: The effect of treatment compounds on the adhesion of normal RBCs to the endothelial layer.

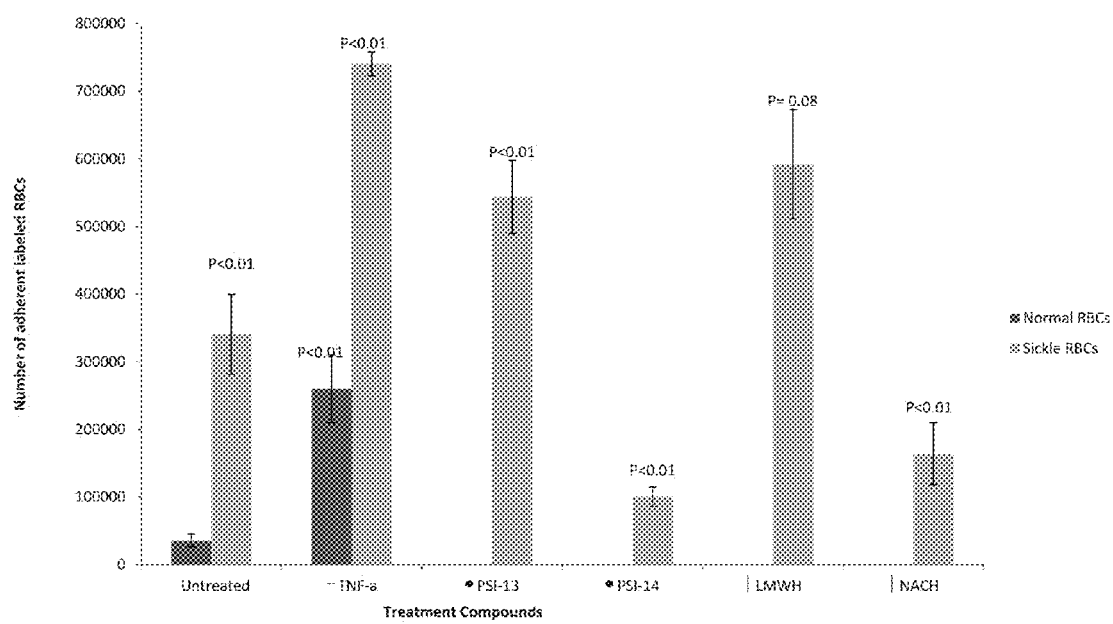
Figure 6: The effect of treatment compounds on the adhesion of sickle RBCs to the endothelial layer.

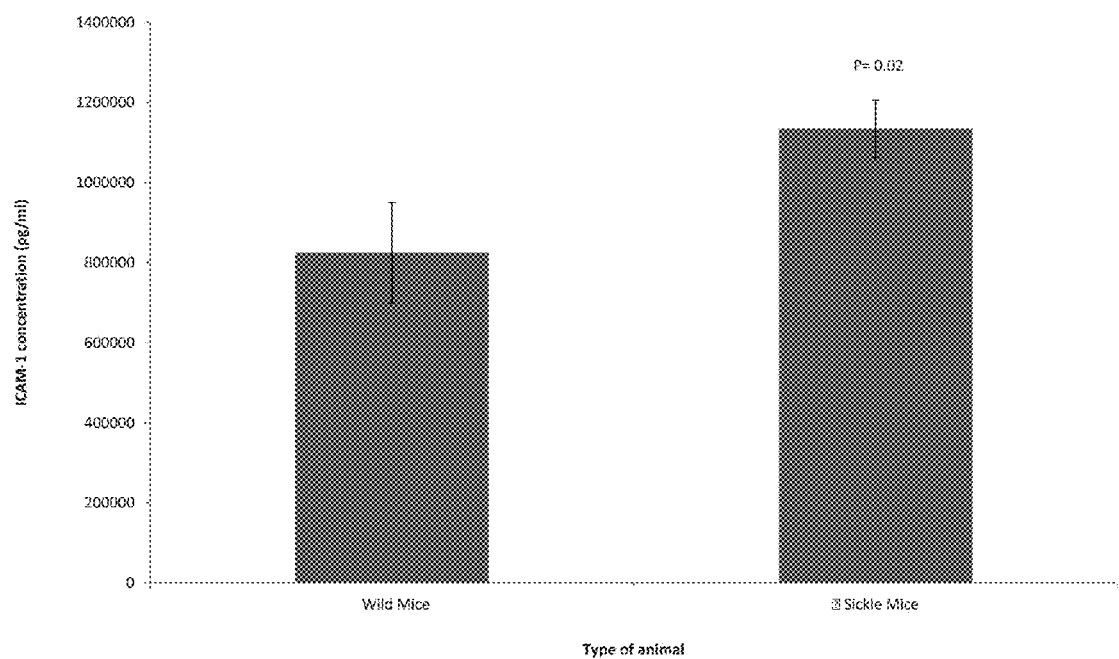
Figure 7: ICAM-1 levels in the plasma of wild mice (n= 4) in comparison to transgenic sickle cell mice (n= 4).

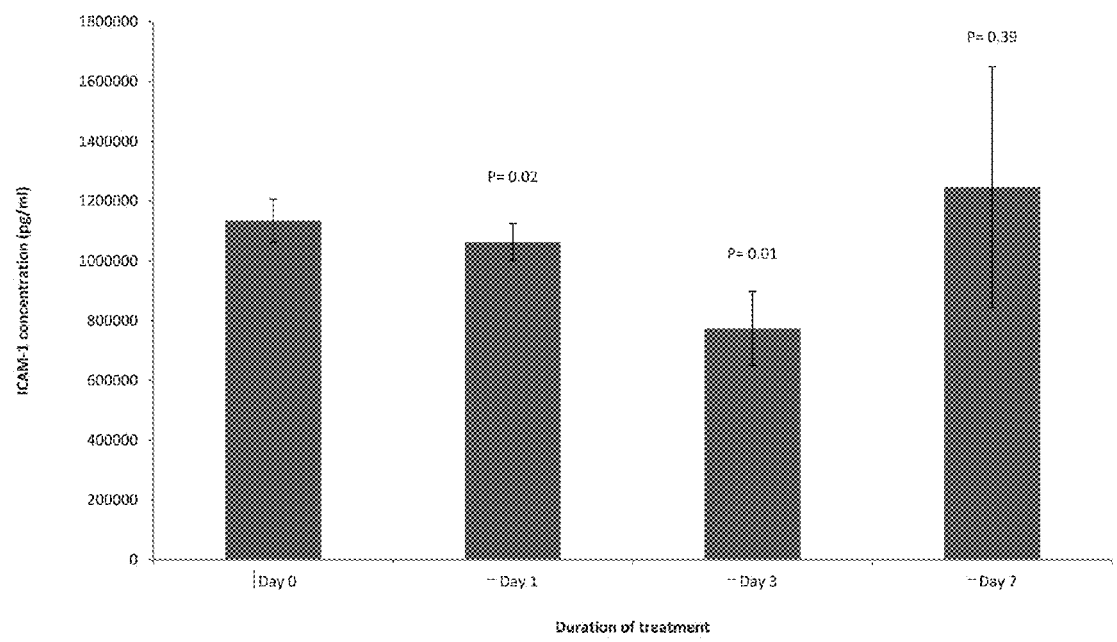
Figure 8: ICAM-1 levels in the plasma of transgenic sickle cell mice (n= 4) after daily treatment with LMWH (5 mg/kg) for 7 days.

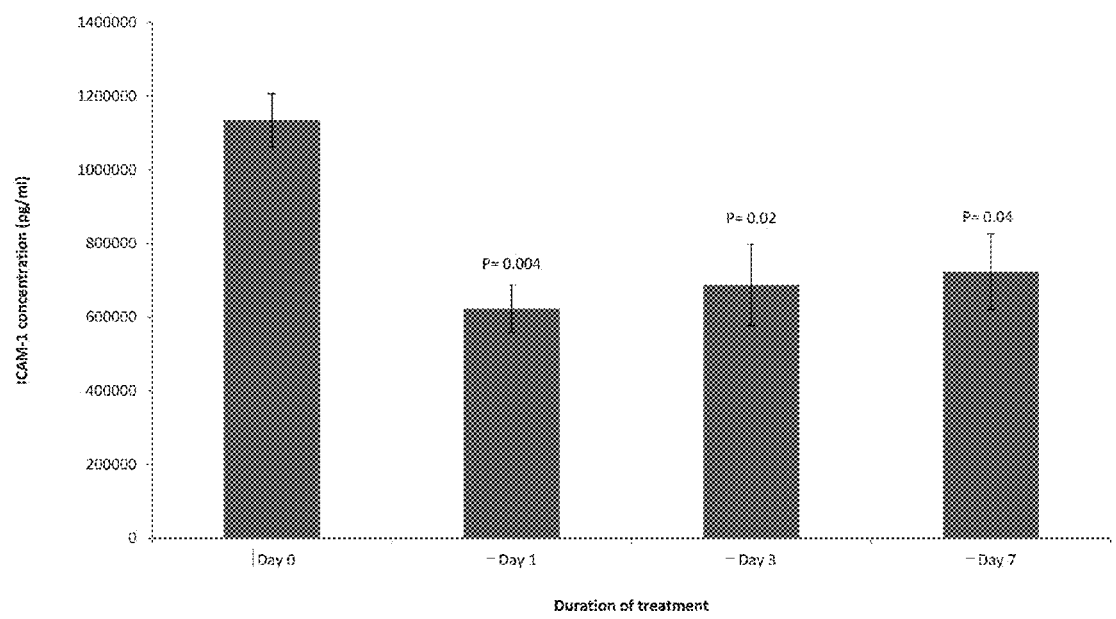
Figure 9: ICAM-1 levels in the plasma of transgenic sickle cell mice (n= 4) after daily treatment with NACH (20 mg/kg) for 7 days.

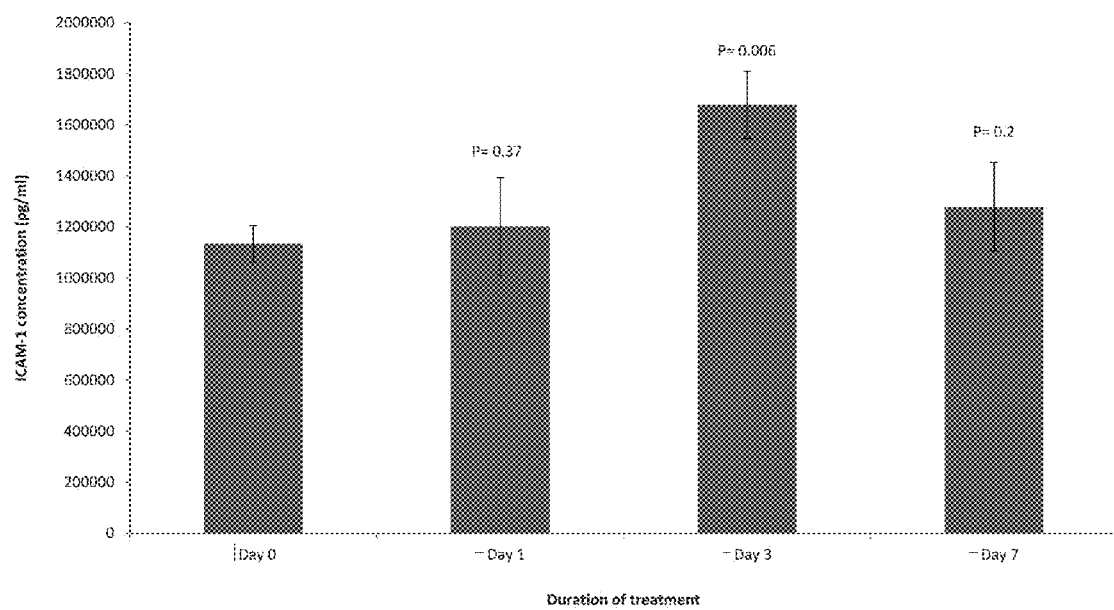
Figure 10: ICAM-1 levels in the plasma of transgenic sickle cell mice (n= 4) after daily treatment with PSI-14 (10 mg/kg) for 7 days.

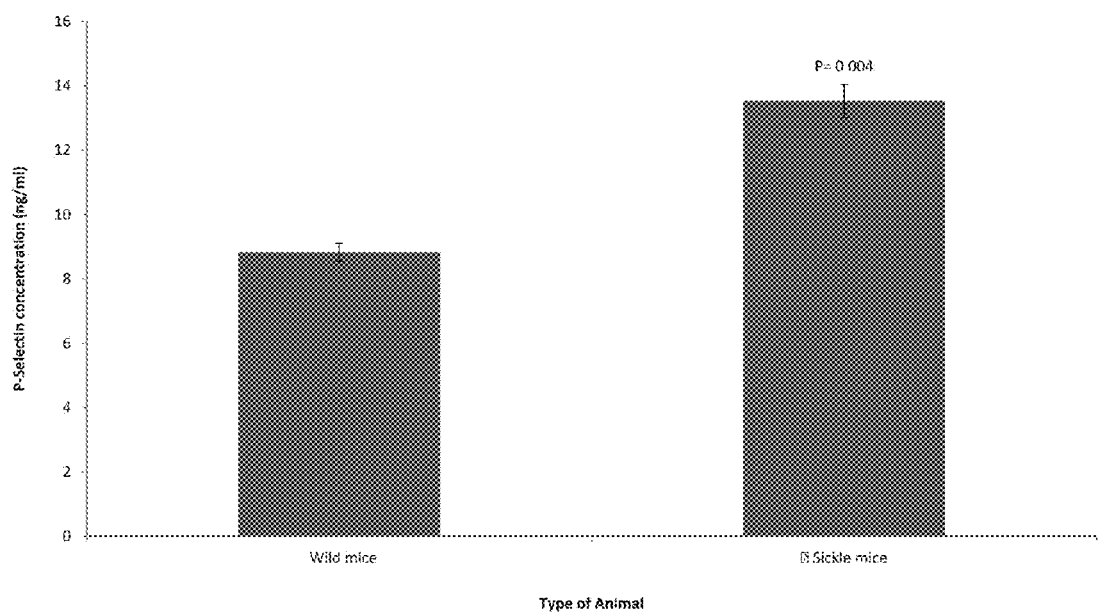
Figure 11: P-selectin levels in the plasma of wild mice (n= 4) in comparison to transgenic sickle cell mice (n= 4).

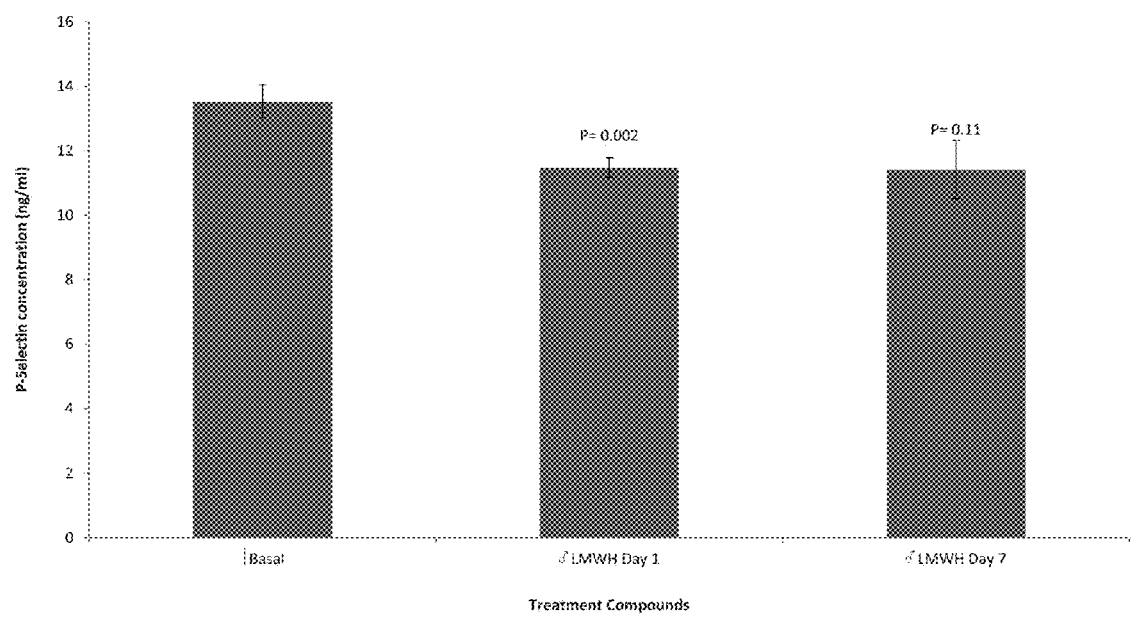
Figure 12: P-selectin levels in the plasma of transgenic sickle cell mice (n= 4) after daily treatment with LMWH (5 mg/kg) for 7 days.

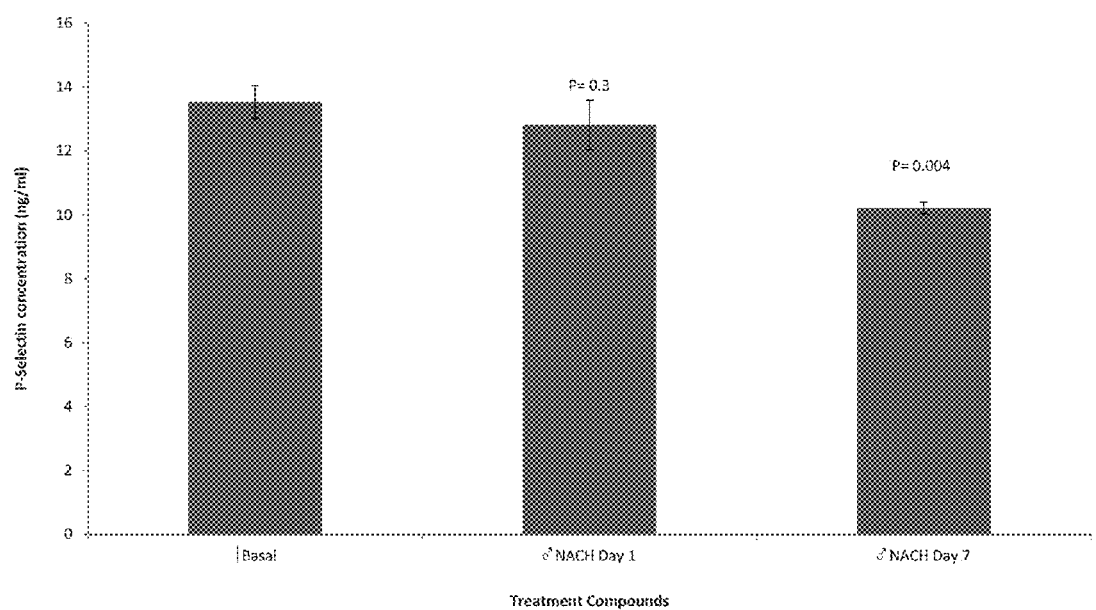
Figure 13: P-selectin levels in the plasma of transgenic sickle cell mice (n= 4) after daily treatment with NACH (20 mg/kg) for 7 days.

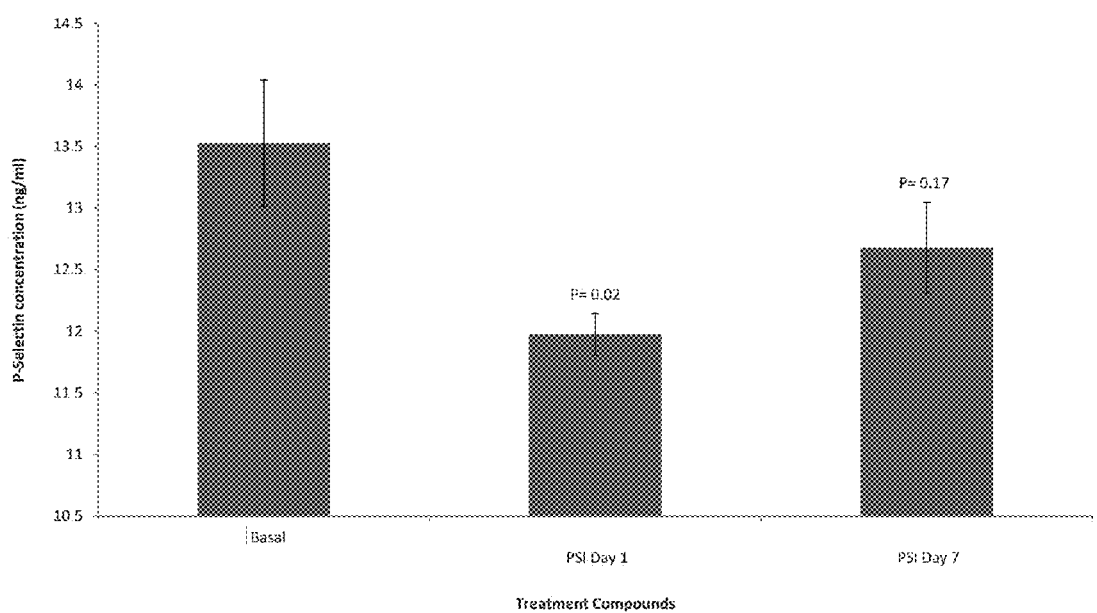
Figure 14: P-selectin levels in the plasma of transgenic sickle cell mice (n= 4) after daily treatment with PSI-14 (10 mg/kg) for 7 days.

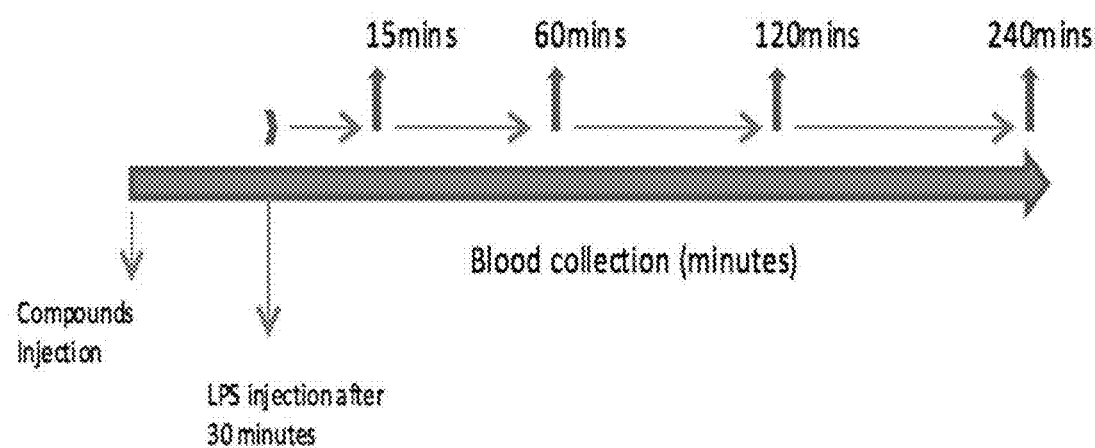
Figure 15: Experimental protocol for LPS administration with or without SNACH and blood collection time line for cytokine and chemokine measurements.

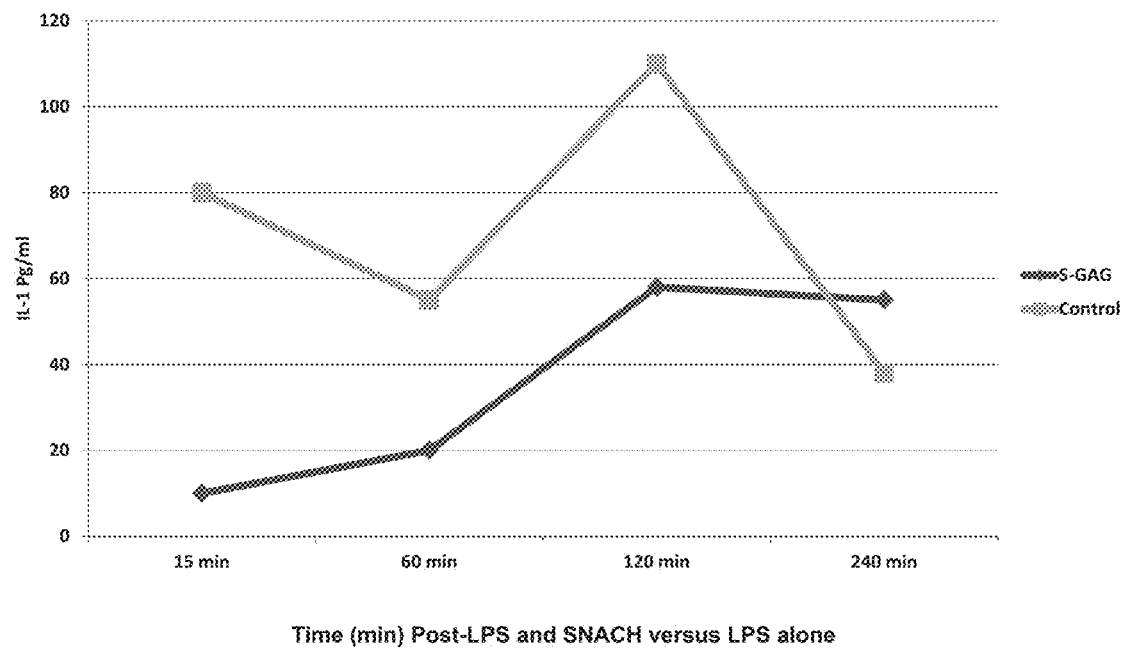
Figure 16: Effect of SNACH on LPS –mediated IL-1 beta elevation

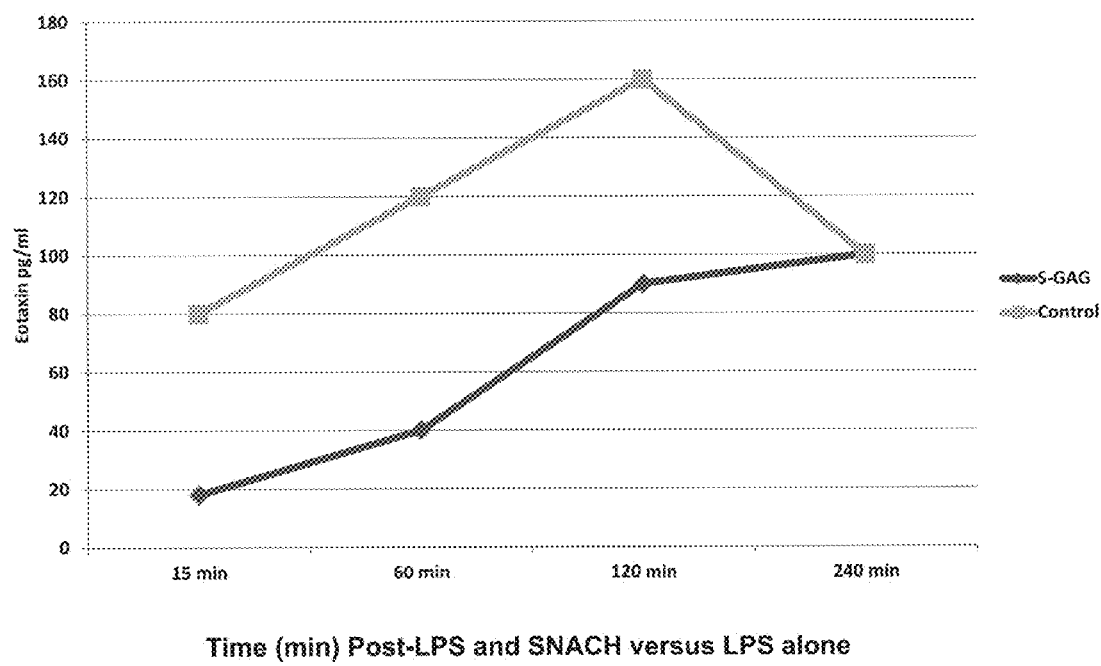
Figure 17: Effect of SNACH on LPS –mediated elevation of Eotaxin

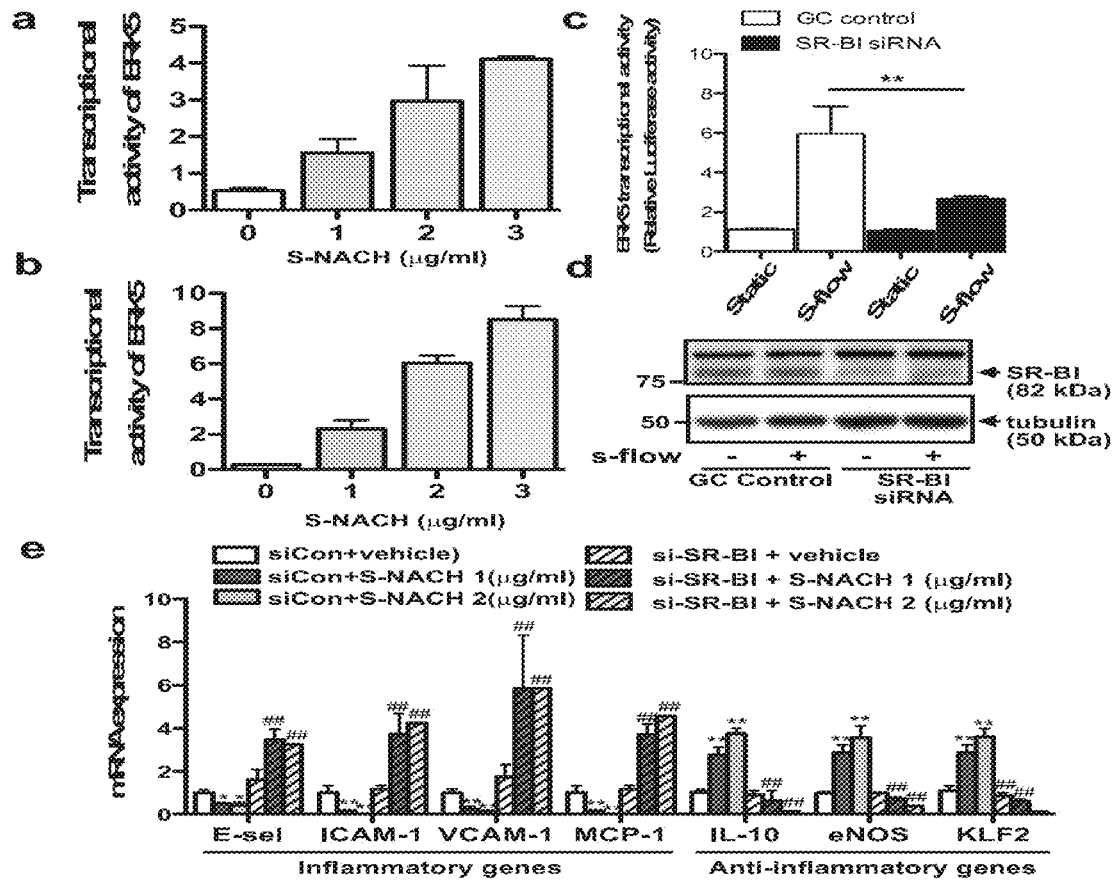
Figure 18: S-NACH and steady laminar flow (s-flow) increased ERK5 transcriptional activity, and crucial role of SR-BI in regulating s-flow and S-NACH-induced ERK5 transcriptional activity and down-regulation of inflammatory genes and up-regulation of anti-inflammatory genes expression

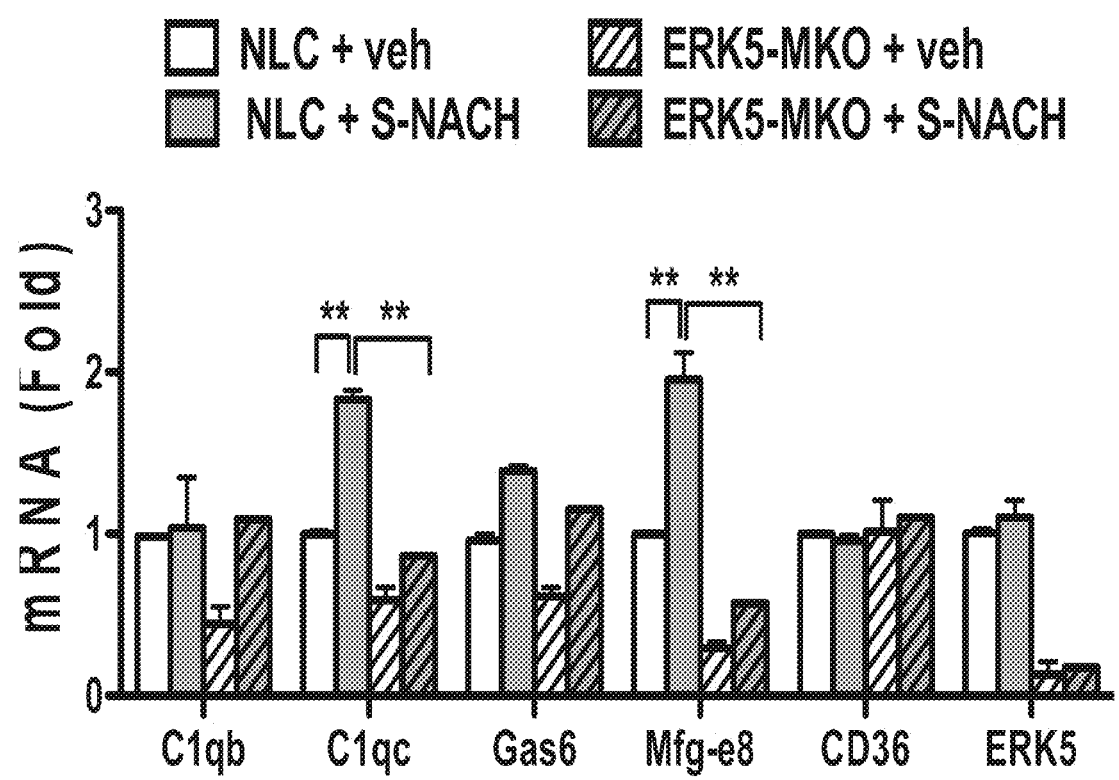
Figure 19: S-NACH increased C1qc and Mfg-e8 via ERK5

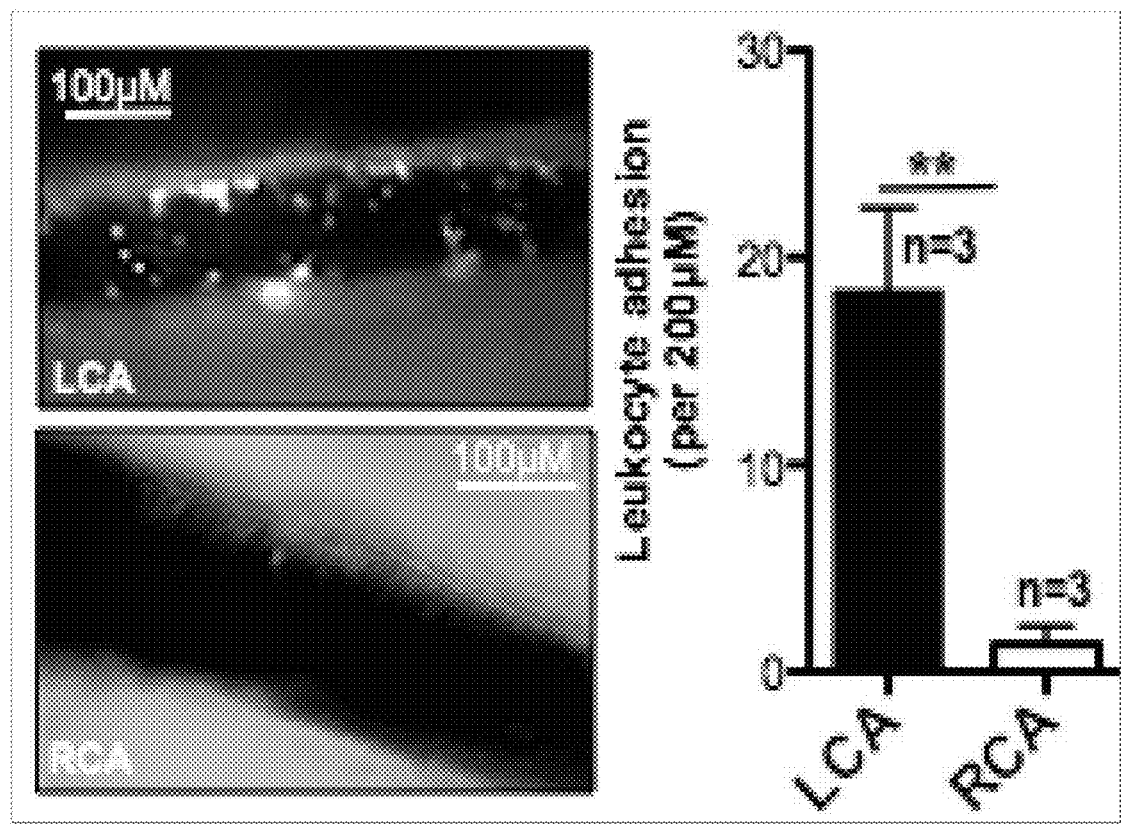
Figure 20: Leukocyte adhesion in carotid artery after partial ligation of the left carotid artery (LCA)

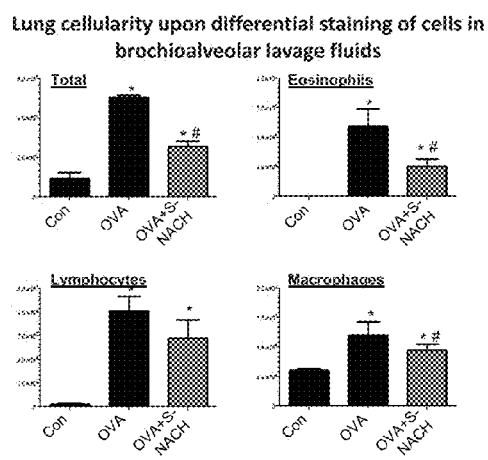
Figure 21: Effect of S-NACH on Ovalbumin antigen (OVA) challenge mediated- lung injury.

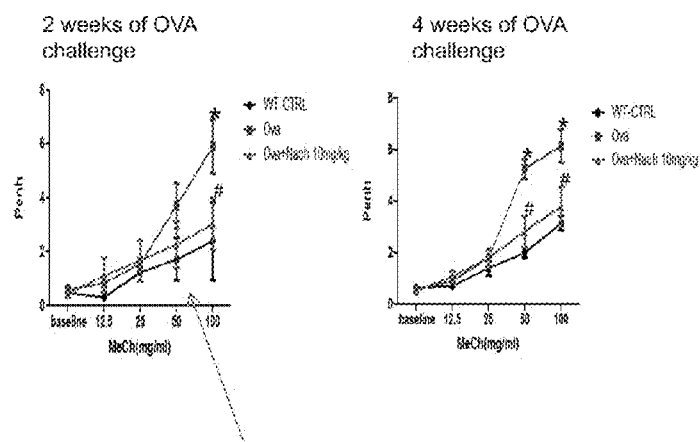
Figure 22: The Effect of SNACH on airway hypersensitivity to Methacholine: S-NACH group reacted in a pattern similar to that of the unchallenged group.

Collagen Assay:
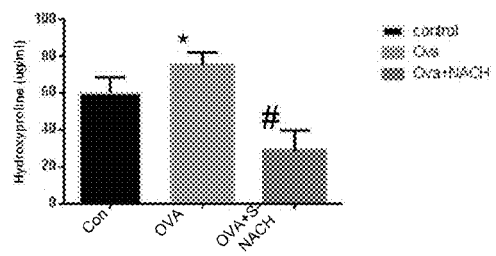
Figure 23: Effect of S-NACH on OVA-mediated Collagen Lung tissues increase: Lung tissues were hydrolyzed and then hydroxyproline was measured using a colorimetric assay.

METHOD AND COMPOSITION OF GLYCOSAMINOGLYCANS IN SICKLE CELL AND VASCULAR DISORDERS

RELATED APPLICATIONS

The present invention claims priority to U.S. Provisional No. 61/896,876, filed on Oct. 29, 2013, which is incorporated herein by reference in its entirety.

TECHNICAL FIELD

The present invention relates to compositions and associated methods for the prevention and treatment of various vascular disorders and associated complications by use of sulfated or super-sulfated non-anticoagulant low molecular weight heparin (SNACH or S-SNACH, respectively) and their nanoformulations.

BACKGROUND

Vascular disorders include atherosclerosis, Sickle cell, Scleroderma and associated organ complications. Sickle cell disease (SCD) is one of the most common monogenic disorders where more than 250,000 children affected with SCD are born each year worldwide. See Roberts I, De montalembert M, Sickle cell disease as a paradigm of immigration hematology: new challenges for hematologists in Europe, Haematologica, 2007; 92(7):865-71. See Weatherall D J, Clegg J B., Inherited haemoglobin disorders: an increasing global health problem, Bull World Health Organ, 2001; 79(8):704-12.

SCD has the widest distribution throughout sub-Saharan Africa, India and the Middle East. See Weatherall D J, Clegg J B., Inherited haemoglobin disorders: an increasing global health problem, Bull World Health Organ, 2001; 79(8):704-12.

It is estimated that the prevalence of the SCD trait in Saudi Arabia is 4.2%. In the US it affects about 72,000 people, and 2 million people are carriers, most of whom are African Americans. See Alhamdan N A, Almazrou Y Y, Alswaidi F M, Choudhry A J, Premarital screening for thalassemia and sickle cell disease in Saudi Arabia. Genet Med., 2007; 9(6):372-7. See Creary M, Williamson D, Kulkarni R., Sickle cell disease: current activities, public health implications, and future directions, J Womens Health (Larchmt), 2007; 16(5):575-82.

Owing to advances in health care, better nutrition, and infection control, there has been a reduction in children's mortality and consequently an increased prevalence of SCD and hemoglobin disorders. See Weatherall D J, Clegg J B., Inherited haemoglobin disorders: an increasing global health problem, Bull World Health Organ, 2001; 79(8):704-12.

The SCD burden on patients is manifested by the acute and chronic complications of the disease such as painful crises, acute chest syndrome, stroke, and multi-organ failure. Additionally, vasoocclusive crisis with high pain rates is a major risk factor for early death. See Platt O S, Brambilla D J, Rosse W F, et al. Mortality in sickle cell disease. Life expectancy and risk factors for early death. N Engl J. Med., 1994; 330(23):1639-44.

Other risks include aplastic crises, splenic sequestration, and cerebrovascular accidents. A recent study showed that 48% of SCD patients had documented, irreversible organ damage by the fifth decade, including pulmonary hypertension, stroke and end stage renal disease. See Powers D R, Chan L S, Hiti A, Ramicone E, Johnson C., Outcome of sickle cell anemia: a 4-decade observational study of 1056 patients, Medicine (Baltimore), 2005; 84(6):363-76.

Nowadays, current treatment strategies for SCD involve the use of chronic blood transfusion, hydroxyurea, and bone marrow transplantation. These treatments might have strong evidence for their role in the disease management, but obviously are not without significant side effects. Patients who are receiving chronic blood transfusions are at high risk of infection, immunologic reactions and iron overload. Additionally, it might be not feasible for children and their families to keep in good compliance on this treatment, since it requires a long term commitment and includes many hazardous side effects. Leukemia has been reported after long-term treatment with hydroxyurea, in addition to neutropenia and thrombocytopenia. Bone marrow transplantation is the only curative treatment for SCD, but not the optimal practical strategy. It needs a well-matched donor and carries the risk of graft rejection and neurologic complications.

With respect to Hemoglobin Polymerization, the primary event in SCD molecular pathogenesis is polymerization of deoxygenated hemoglobin S (HbS). See Bunn H F., Pathogenesis and treatment of sickle cell disease, N Engl J. Med., 1997; 337(11):762-9.

Owing to the presence of valine in the β-globin chain, deoxygenated HbS will make a hydrophobic interaction via valine with complementary sites on a neighboring hemoglobin molecule, triggering an aggregation of hemoglobin molecules into large polymers. This mechanism distorts the shape of the red blood cells (RBCs) and decreases its deformability, leading to the formation of rigid sickle cells. These cells will lead to vasoocclusive crisis development, one of the major complications of SCD. See Bunn H F., Pathogenesis and treatment of sickle cell disease, N Engl J. Med., 1997; 337(11):762-9. See Gabriel A, Przybylski J., Sickle-cell anemia: A Look at Global Haplotype Distribution, Nature Education, 2010; 3(3):2-12.

With respect to Abnormal Adhesion to Vascular Endothelium, sickle red blood cells interact abnormally with the vascular endothelium, and this is thought to be one of the primary initiating factors in the development of microvascular occlusions in SCD. See Hebbel R P, Yamada O, Moldow C F, Jacob H S, White J G, Eaton J W., Abnormal adherence of sickle erythrocytes to cultured vascular endothelium: possible mechanism for microvascular occlusion in sickle cell disease, J Clin Invest., 1980; 65(1):154-60.

Sickle erythrocytes stay persistently bound to the endothelium despite an increase in shear force inside the vessels, which is opposite to the behavior of normal RBCs. There are probably multiple interaction mechanisms contributing to the adhesion, either directly or through bridging protein.

Two pathways may explain the consequences of sickle RBCs' abnormal interaction. First, the sickle, rigid cells are trapped inside the vessels, which leads to polymerization of HbS and obstructs the arteries. See Bunn H F., Pathogenesis and treatment of sickle cell disease, N Engl J. Med., 1997; 337(11):762-9. Second, sickle cells' adhesion increases the activity of the nuclear factor κB and endothelin-1, and upregulates vascular cell adhesion molecule (VCAM) and intercellular adhesion molecule (ICAM) adhesion molecules' activity, (see Mosseri M, Bartlett-pandite A N, Wenc K, Isner J M, Weinstein R., Inhibition of endothelium-dependent vasorelaxation by sickle erythrocytes, Am Heart J., 1993; 126(2):338-46) (see Phelan M, Perrine S P, Brauer M, Faller D V, Sickle erythrocytes, after sickling, regulate the expression of the endothelin-1 gene and protein in human endothelial cells in culture, J Clin Invest., 1995; 96(2):1145-51) which result in vessel wall injury, remodeling, and occlusion.

With respect to Inflammation, Vascular disorders include atherosclerosis, Sickle cell, Scleroderma and associated organ complications. There is evidence that inflammation plays a major role in the development of the vasoocclusive complications associated with SCD. This collectively triggers the production of cytokines, leading to upregulation of proinflammatory cells and activation of the inflammatory responses and ultimately to further vascular injury. Additionally, NO function in reducing the inflammatory mediators may contribute to the development of cerebrovascular disease in sickle cell anemia, because nitric oxide is low in these patients. It has been suggested that hydroxyurea might have a role in SCD treatment by decreasing the neutrophil count, but this area needs further research.

With respect to Hemolysis, Reperfusion Injury and Nitric Oxide, it is well known that hemolysis plays an integral part in sickle cell anemia. Its role is due to the accumulation of cell-free hemoglobin, leading to NO conversion to the inactive metabolites nitrate and methemoglobin, (see Olson J S, Foley E W, Rogge C, Tsai A L, Doyle M P, Lemon D D., No scavenging and the hypertensive effect of hemoglobin-based blood substitutes, Free Radic Biol Med., 2004; 36(6):685-97) making it ineffective in controlling vessel tone. Hemolysis also is leading to depletion of NO by overwhelming the removal system.

Recurrent episodes of vasoocclusion and reperfusion play a major role in the pathogenesis of vascular injury in sickle cell anemia. Studies showed that reperfusion injury is due to transcription factors activation, leucocytes adhesion, and production of free radicals in the endothelium. See Kaul D K, Hebbel R P., Hypoxia/reoxygenation causes inflammatory response in transgenic sickle mice but not in normal mice, J Clin Invest., 2000; 106(3):411-20.

Consequently, release of toxic free radicals due to oxidative stress (see Mcbride A G, Borutaite V, Brown G C., Superoxide dismutase and hydrogen peroxide cause rapid nitric oxide breakdown, peroxynitrite production and subsequent cell death, Biochim Biophys Acta., 1999; 1454(3): 275-88) leads to decreased availability of nitric oxide in the blood stream. All of this leads to vasoconstriction and platelet aggregation, and contributes to vascular dysfunction in SCD.

With respect to Hyper-coagulation, activation of the coagulation system is significant in SCD pathogenesis. Studies showed that patients with SCD are more likely to have ischemic stroke and pulmonary embolism due to thrombosis development. These patients' high level of D-dimer, antithrombin III, plasmin: antiplasmin complex, and low levels of proteins C and S in the bloodstream make the role of coagulation factors obvious. See Francis R B., Elevated fibrin D-dimer fragment in sickle cell anemia: evidence for activation of coagulation during the steady state as well as in painful crisis, Haemostasis, 1989; 19(2):105-11. See Tomer A, Harker L A, Kasey S, Eckman J R., Thrombogenesis in sickle cell disease, J Lab Clin Med., 2001; 137(6):398-407.

Additionally, in sickle cell patients there is evidence of platelet activation and monocytes' abnormal expression of tissue factor. See Shet A S, Aras O, Gupta K, et al., Sickle blood contains tissue factor-positive microparticles derived from endothelial cells and monocytes, Blood, 2003; 102(7): 2678-83.

Exposure of phosphatidylserine of sickle cell's membrane is another factor that might contribute to the hyper-coaguable state by activation of prothrombin.

BRIEF SUMMARY

The present invention provides a composition comprising a nanoparticle. The nanoparticle comprises a shell which encapsulates sulfated non-anticoagulant heparin (SNACH). The shell comprises poly L-arginine. The SNACH is ionically or covalently bonded to the poly L-arginine. A method for treating a disorder of a subject includes: administering to the subject a therapeutically effective amount of the composition for treating the disorder. The disorder is a vascular disorder, a complication of the vascular disorder, or a combination thereof.

BRIEF DESCRIPTION OF THE DRAWINGS

FIG. 4 depicts adherence of normal and sickle red blood cells (RBCs) adhesion to endothelial cells (ECs) with or without TNF-α treatment, in accordance with embodiments of the present invention.

FIG. 5 depicts the effect of treatment compounds on the adhesion of normal RBCs to the endothelial layer, in accordance with embodiments of the present invention.

FIG. 6 depicts the effect of treatment compounds on the adhesion of sickle RBCs to the endothelial layer, in accordance with embodiments of the present invention.

FIG. 7 depicts ICAM-1 levels in the plasma of wild mice (n=4) in comparison to transgenic sickle cell mice (n=4), in accordance with embodiments of the present invention. The plasma of transgenic sickle mice used in this study showed significantly higher levels of ICAM-1.

FIG. 8 depicts ICAM-1 levels in the plasma of transgenic sickle cell mice (n=4) after daily treatment with LMWH (5 mg/kg) for 7 days), in accordance with embodiments of the present invention.

FIG. 9 depicts ICAM-1 levels in the plasma of transgenic sickle cell mice (n=4) after daily treatment with NACH (20 mg/kg) for 7 days, in accordance with embodiments of the present invention.

FIG. 10 depicts ICAM-1 levels in the plasma of transgenic sickle cell mice (n=4) after daily treatment with PSI-14 (10 mg/kg) for 7 days, in accordance with embodiments of the present invention.

FIG. 11 depicts P-selectin levels in the plasma of wild mice (n=4) in comparison to transgenic sickle cell mice (n=4), in accordance with embodiments of the present invention.

FIG. 12 depicts P-selectin levels in the plasma of transgenic sickle cell mice (n=4) after daily treatment with LMWH (5 mg/kg) for 7 days, in accordance with embodiments of the present invention.

FIG. 13 depicts P-selectin levels in the plasma of transgenic sickle cell mice (n=4) after daily treatment with NACH (20 mg/kg) for 7 days, in accordance with embodiments of the present invention.

FIG. 14 depicts P-selectin levels in the plasma of transgenic sickle cell mice (n=4) after daily treatment with PSI-14 (10 mg/kg) for 7 days, in accordance with embodiments of the present invention.

FIG. 15 depicts Protocol for Examining the Effect of SNACH on LPS-mediated inflammation, in accordance with embodiments of the present invention.

FIG. 16 depicts an effect of SNACH on LPS-mediated increase in IL-1 beta-LPS-resulted in a significant increase in the blood levels of IL-beta over 240 minutes, which were significantly suppressed by SNACH treatment, in accordance with embodiments of the present invention.

FIG. 17 depicts an effect of SNACH on LPS-mediated increase in Eotaxin-LPS-resulted in a significant increase in the blood levels of Eotaxin over 240 minutes, which were significantly suppressed by SNACH treatment, in accordance with embodiments of the present invention.

FIG. 18 depicts SNACH and steady laminar flow (s-flow) increased ERK5 transcriptional activity, and crucial role of SR-BI in regulating s-flow and SNACH-induced ERK5 transcriptional activity and down-regulation of inflammatory genes and up-regulation of anti-inflammatory genes expression, in accordance with embodiments of the present invention.

FIG. 19 depicts SNACH increased C1qc and Mfg-e8 via ERK5, in accordance with embodiments of the present invention.

FIG. 20 depicts leukocyte adhesion in carotid artery after partial ligation of the left carotid artery (LCA), in accordance with embodiments of the present invention.

FIG. 21 depicts an effect of SNACH on Ovalbumin antigen (OVA) challenge mediated-lung injury, in accordance with embodiments of the present invention.

FIG. 22 depicts an effect of SNACH on airway hypersensitivity to Methacholine: SNACH group reacted in a pattern similar to that of the unchallenged group, in accordance with embodiments of the present invention.

FIG. 23 depicts an effect of SNACH on OVA-mediated Collagen Lung tissues increase: Lung tissues were hydrolyzed and then hydroxyproline was measured using a colorimetric assay, in accordance with embodiments of the present invention.

DETAILED DESCRIPTION

Figure 1:
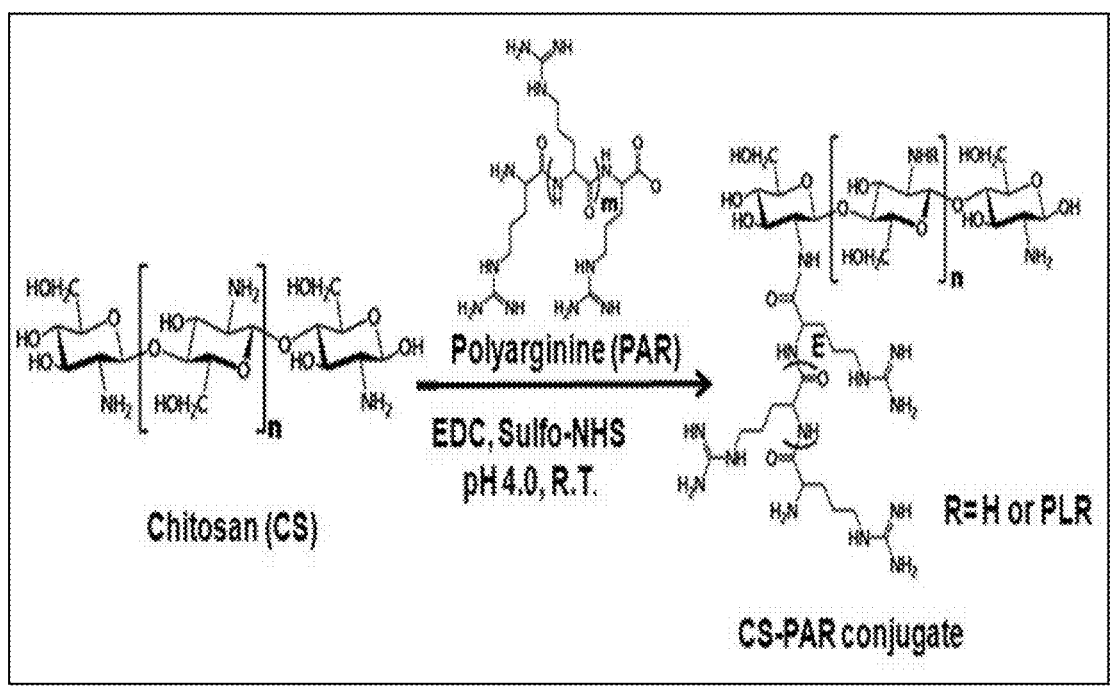
FIG. 1 is a schematic diagram showing the synthesis of Chitosan-poly L-arginine conjugate, in accordance with embodiments of the present invention.

The present invention aims to develop novel therapies based on understanding of the disease pathophysiology. The present invention considers heparin derivatives to be excellent examples since heparin derivatives affect almost every aspect of Sickle cell disease (SCD) pathogenesis. The present invention uses Glycosaminoglycans (GAGs) such as: tinzaparin, a low-molecular weight heparin (LMWH); novel sulfated non-anticoagulant heparin (SNACH); and their nanoformulations versus specific P-selectin inhibitor (PSI). Studies of the effect of these compounds on the adhesion of red blood cells (RBCs) to endothelial cells (ECs) using in vitro adhesion assay were conducted. Additionally, a transgenic SCD mouse model was used to test these compounds' effect on the intercellular adhesion molecule-1 (ICAM-1) as an adhesion biomarker. The studies showed the advantage of SNACH over LMWH by its minimum effect on hemostasis and bleeding. Additionally, PSI is effective in inhibiting sickle cell adhesion to endothelium, which is one of the major initiating events in SCD pathogenesis.

Definitions: low sulfated Non-anticoagulant Low Molecular Weight Heparin (NACH) has a sulfate/carboxylate ratio in a range of 1.5 to 2.4/1, SNACH has a sulfate/carboxylate ratio in a range of greater than 2.4 to 3.5/1, and S—SNACH has a sulfate/carboxylate ratio in a range of greater than 3.5 to 5.0/1. The preceding sulfate/carboxylate ratio is a ratio of the number of sulfate groups to the number of carboxylate groups.

A major challenge in sickle cell anemia is the complexity of pathogenesis, which makes it not fully understood. The most important factors that play a role in the clinical picture are endothelial adhesion, vascular tone, inflammation, procoagulation, and nitric oxide (NO) depletion. The bright side of this is that as more is learned about SCD pathophysiology, more options become available for interventional-targeted therapy to reduce the disease morbidity and mortality.

For vascular disorders such as the case in atherosclerosis, sickle cells are also associated with inflammation leading to various organ dysfunctions such as the case in acute and chronic pulmonary dysfunctions. Abnormal cellular adhesion is one of the primary initiating factors in the development of atherosclerosis, sickle cell disease (SCD) complications, especially acute vasoocclusive crisis. Both endothelial cell and red blood cell abnormal adhesion leading to dysfunction reflected by the shedding of intercellular adhesion molecule-1 (ICAM-1) and P-selectin were documented in SCD. Similarly, excessive leukocytes and sickle red blood cells (RBCs) adhesion to endothelium, which are increased in response to different inflammatory stimuli in atherosclerosis and SCD. The modulatory effects of novel glycosaminoglycans mainly sulfated non-anticoagulant heparin (SNACH) and P-selectin inhibitor (PSI), on the process of sickle erythrocyte-endothelium adhesion were documented. Using PKH67 labeled RBCs, static adhesion assays were conducted on human umbilical vein endothelial cells (HUVECs) and showed significant higher adhesion of sickle RBCs compared to normal RBCs. Pretreatment of both erythrocytes and endothelium with SNACH or PSI showed statistically significant inhibitory effect on sickle RBCs adhesion. Measurement of the adhesion biomarkers such as soluble ICAM-1 and P-selectin showed significantly higher levels in the plasma of sickle cell mice compared to wild type mice. Treatment studies of cell sickle mice SNACH or the LMWH tinzaparin showed a distinct decrease in the shedding of soluble ICAM-1 and P-selectin levels over time post-treatment, with higher inhibitory effect by SNACH as compared to tinzaparin. In contrast, PSI treatment of sickle mice showed a decrease in soluble P-selectin levels over time of treatment with no effect on soluble ICAM-1 levels. SNACH did not have any effect on bleeding time or aPTT in contrast to the LMWH tinzaparin, which resulted in significant increase in aPTT and bleeding time. Our results demonstrate the distinct efficacy and safety of SNACH in inhibiting the abnormal adhesion in SCD, without any effect on hemostasis. Vascular disorders include atherosclerosis, Sickle cell, pulmonary hypertension, scleroderma and associated organ complications.

FIG. 1 is a schematic diagram showing the synthesis of Chitosan-poly L-arginine conjugate, in accordance with embodiments of the present invention.

Figure 2:
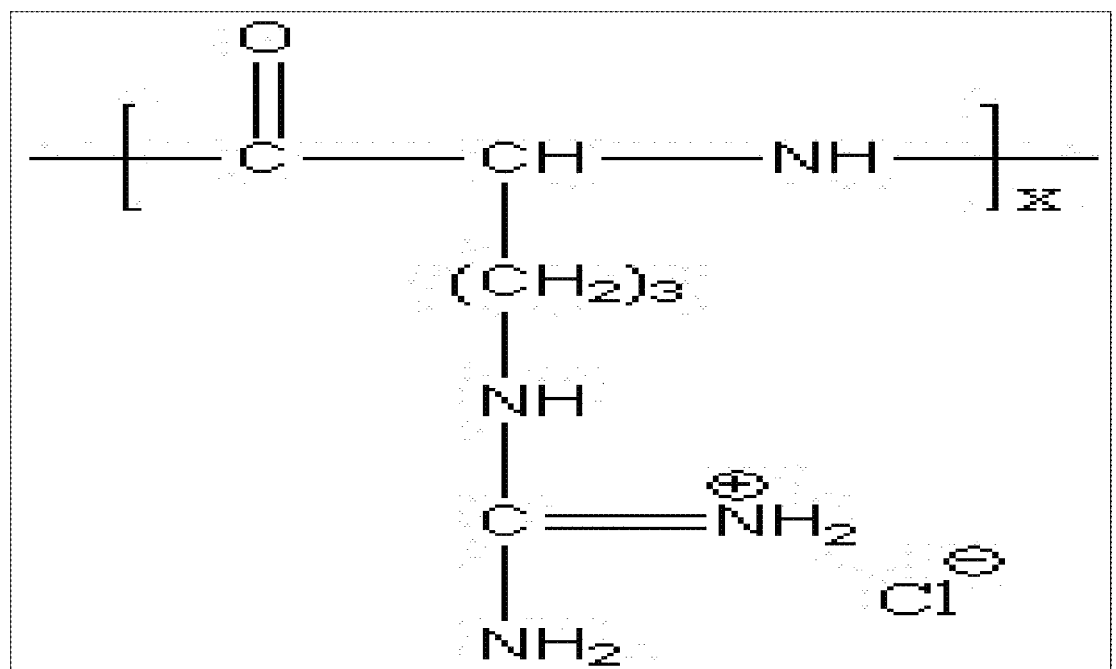
FIG. 2 depicts L-Arginine Structure and Number of Arginine Repeating Units: x=10-100 (poly-L-arginine, MW=2,000-20,000 Da), in accordance with embodiments of the present invention.

FIG. 2 depicts L-Arginine Structure and Number of Arginine Repeating Units: x=10-100 (poly-L-arginine, MW=2,000-20,000 Da), in accordance with embodiments of the present invention.

Figure 3:
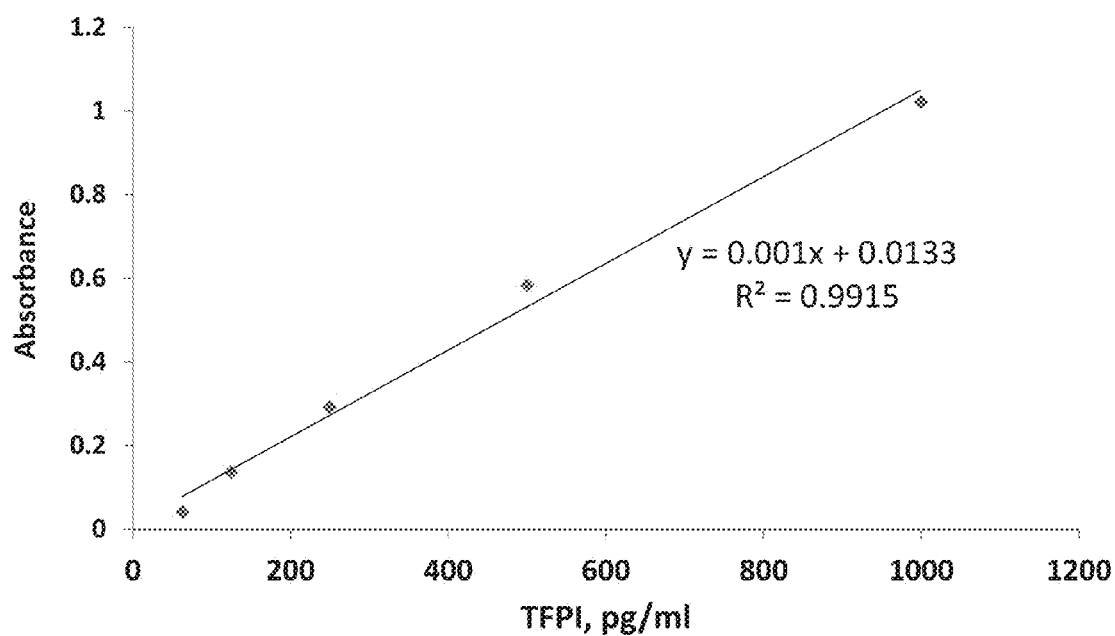
FIG. 3 depicts a TFPI Calibration Curve illustrating a linear relationship between wide ranges of TFPI and absorbance, in accordance with embodiments of the present invention.

FIG. 3 depicts a TFPI Calibration Curve illustrating a linear relationship between wide ranges of TFPI and absorbance, in accordance with embodiments of the present invention.

FIG. 4 depicts adherence of normal and sickle red blood cells (RBCs) adhesion to endothelial cells (ECs) with or without TNF-α treatment, in accordance with embodiments of the present invention. Normal cells did not show any significant adherence to EC. In contrast, sickle RBCs demonstrated significantly higher adhesion by almost 10-fold. By treating ECs with 10 ng/ml of TNF-α to induce the expression of adhesion molecules, both types of RBCs showed significant increase in adhesion with higher values in sickle RBCs. The error bars show the standard deviations of the mean adherence values. Normal cells did not show any significant adherence to EC. In contrast, sickle RBCs demonstrated significantly higher adhesion by almost 10 folds. By treating ECs with 10 ng/ml of TNF-α to induce the expression of adhesion molecules, both types of RBCs showed significant increase in adhesion with higher values in sickle RBCs.

FIG. 5 depicts the effect of treatment compounds on the adhesion of normal RBCs to the endothelial layer, in accordance with embodiments of the present invention. PSI-14 treatment significantly decreased the adhesion of normal RBCs by more than 75% when compared to TNF-α only (positive control). PSI-13, LMWH, and NACH also decreased the adhesion by 20-35% but the results were statistically insignificant. The error bars show the standard deviations of the mean adherence values.

FIG. 6 depicts the effect of treatment compounds on the adhesion of sickle RBCs to the endothelial layer, in accordance with embodiments of the present invention. Adding PSI-14 or NACH significantly decreased the adhesion of sickle RBCs when compared to TNF-α only (positive control). In contrast, LMWH did not show a decrease in the adhesion that could be considered statistically significant. The error bars show the standard deviations of the mean adherence values.

FIG. 7 depicts ICAM-1 levels in the plasma of wild mice (n=4) in comparison to transgenic sickle cell mice (n=4), in accordance with embodiments of the present invention. The plasma of transgenic sickle mice used in this study showed significantly higher levels of ICAM-1.

FIG. 8 depicts ICAM-1 levels in the plasma of transgenic sickle cell mice (n=4) after daily treatment with LMWH (5 mg/kg) for 7 days, in accordance with embodiments of the present invention. Levels of ICAM-1 at multiple time points showed a decrease only on the first and third days of treatment, and the results were statistically significant.

FIG. 9 depicts ICAM-1 levels in the plasma of transgenic sickle cell mice (n=4) after daily treatment with NACH (20 mg/kg) for 7 days, in accordance with embodiments of the present invention. Levels of ICAM-1 at multiple time points showed a linear decrease over time of treatment. The results were statistically significant for all days of treatment. Using One-way ANOVA analysis validated the significance of the results with $P<0.05$.

FIG. 10 depicts ICAM-1 levels in the plasma of transgenic sickle cell mice (n=4) after daily treatment with PSI-14 (10 mg/kg) for 7 days, in accordance with embodiments of the present invention. Levels of ICAM-1 in multiple time points did not show any decrease over time of treatment, and the results were statistically insignificant. Using One-way ANOVA calculations validated the insignificance of the results with P value >0.05.

FIG. 11 depicts P-selectin levels in the plasma of wild mice (n=4) in comparison to transgenic sickle cell mice (n=4), in accordance with embodiments of the present invention. The plasma of transgenic sickle mice used in this study significantly showed more than 50% higher levels of P-selectin.

FIG. 12 depicts P-selectin levels in the plasma of transgenic sickle cell mice (n=4) after daily treatment with LMWH (5 mg/kg) for 7 days, in accordance with embodiments of the present invention. Levels of ICAM-1 in multiple time points showed a decrease by almost 15%, and the results were statistically significant only in the first day of treatment. Using One-way ANOVA analysis validated the insignificance of the results with P value >0.05.

FIG. 13 depicts P-selectin levels in the plasma of transgenic sickle cell mice (n=4) after daily treatment with NACH (20 mg/kg) for 7 days, in accordance with embodiments of the present invention. Levels of P-selectin in multiple time points showed a linear decrease over time of treatment down by almost 25%. The results were statistically significant only on day 7 of treatment.

FIG. 14 depicts P-selectin levels in the plasma of transgenic sickle cell mice (n=4) after daily treatment with PSI-14 (10 mg/kg) for 7 days, in accordance with embodiments of the present invention. Levels of P-selectin in multiple time points showed a decrease over time of treatment, and the results were statistically significant only at the first day of treatment. Using one-way ANOVA validated the insignificance of the results with P value >0.05.

FIG. 15 depicts Protocol for Examining the Effect of SNACH on LPS-mediated inflammation, in accordance with embodiments of the present invention. SNACH (5 mg/kg, SC) was administered 30 minutes prior to LPS (0.01 mg/kg, IP) versus another group who just received LPS (0.01 mg/kg, IP). Blood samples were collected at different interval over 240 minutes for measurements of IL-beta and Eotaxin.

FIG. 16 depicts an effect of SNACH on LPS-mediated increase in IL-1 beta-LPS-resulted in a significant increase in the blood levels of IL-beta over 240 minutes, which were significantly suppressed by SNACH treatment, in accordance with embodiments of the present invention.

FIG. 17 depicts an effect of SNACH on LPS-mediated increase in Eotaxin-LPS-resulted in a significant increase in the blood levels of Eotaxin over 240 minutes, which were significantly suppressed by SNACH treatment, in accordance with embodiments of the present invention.

FIG. 18 depicts SNACH and steady laminar flow (s-flow) increased ERK5 transcriptional activity, and crucial role of SR-BI in regulating s-flow and SNACH-induced ERK5 transcriptional activity and down-regulation of inflammatory genes and up-regulation of anti-inflammatory genes expression, in accordance with embodiments of the present invention. RAW264.7 cells (a) and HUVECs (b) were transfected with plasmids encoding Gal4-ERK5 and the Gal4-responsive luciferase reporter pG5-Luc. Eighteen hours post transfection; cells were treated with either SNACH or vehicle at final concentration as indicated. (c) HUVECs were transfected with SR-BI siRNA or GC control, and ERK5 transcriptional activity was assayed. (d) HUVECs were transfected by control or SR-BI siRNA for 24 hrs., then cells were treated by SNACH (1 or 2 μg/ml as indicated) for 16 hrs.), and qRT-PCR was used to detect expression of inflammation-related genes as well as IL-10, eNOS, and KLF2 (d). **$p<0.01$, *$p<0.05$.

FIG. 19 depicts SNACH increased C1qc and Mfg-e8 via ERK5, in accordance with embodiments of the present invention. Peritoneal macrophages isolated from NLC or ERK5-MKO mice were treated with SNACH at 1 mg/ml for 18 hrs and qRT-PCR was used to detect expression of indicated opsonins and ERK5. **p<0.01.

FIG. 20 depicts leukocyte adhesion in carotid artery after partial ligation of the left carotid artery (LCA), in accordance with embodiments of the present invention. Three of four caudal branches of LCA in ApoE−/− mice were ligated. Three days after ligation, leukocyte adhesion was detected in LCA as a d-flow model, and the right carotid artery (RCA) as a steady laminar flow model. RCA was dilated more than LCA, Cells stayed over 1 minute.

FIG. 21 depicts an effect of SNACH on Ovalbumin antigen (OVA) challenge mediated-lung injury, in accordance with embodiments of the present invention. SNACH significantly protected the lung against OVA-mediated lung injury.

FIG. 22 depicts an effect of SNACH on airway hypersensitivity to Methacholine: SNACH group reacted in a pattern similar to that of the unchallenged group, in accordance with embodiments of the present invention.

FIG. 23 depicts an effect of SNACH on OVA-mediated Collagen Lung tissues increase. Lung tissues were hydrolyzed and then hydroxyproline was measured using a colorimetric assay, in accordance with embodiments of the present invention. SNACH blocks collagen synthesis or accumulation.

The most important factors that play a role in the clinical picture in sickle cell are endothelial adhesion, vascular tone, inflammation, pro-coagulation, and nitric oxide (NO) depletion. Given these abnormalities, an effective approach was utilized in fixing these alterations with Sulfated-Non Anticoagulant Heparin Derivatives (SNACH) or sulfated Low Molecular Weight heparins (S-LMWH) ionically or covalently complexed with a Poly L-Arginine cross bridged with chitosan (FIG. 1), or combinations of thereof. Poly L-arginine structure and L-arginine repeating units is shown in FIG. 2. Now with novel compositions of the present invention, more options are available for interventional-targeted therapy to reduce vascular disorders and sickle disease morbidity and mortality including injectable, oral or inhalation formulations.

For quantification of TFPI in human endothelial cells, FIG. 3 shows the calibration curve used to calculate the TFP releasing capacity mediated by SNACH.

Initial efforts were directed to optimize the protocol of RBCs adhesion assay. HUVECs monolayer was at least >90% confluent to prevent the adhesion of RBCs to the base of the wells. Blood was collected in EDTA tubes and packed RBCs were used without contamination by platelets or leukocytes as measured by the CBC analyzer. PKH67 labeling of RBCs was uniform, intense, with no leaking or cytotoxicity observed.

Comparing the binding of normal and sickle RBCs to endothelial layer under static conditions, normal cells did not show any significant adherence to endothelial cells (ECs). In contrast, sickle RBCs demonstrated significantly higher adhesion by almost 10-fold. By treating ECs with 10 ng/ml of TNF-α to induce the expression of adhesion molecules, both types of RBCs showed significant increase in adhesion with higher values in sickle RBCs (FIG. 4). Normal cells did not show any significant adherence to EC. In contrast, sickle RBCs demonstrated significantly higher adhesion by almost 10-fold. By treating ECs with 10 ng/ml of TNF-α to induce the expression of adhesion molecules, both types of RBCs showed significant increase in adhesion with higher values in sickle RBCs. The error bars show the standard deviations of the mean adherence values. Normal cells did not show any significant adherence to EC. In contrast, sickle RBCs demonstrated significantly higher adhesion by almost 10 fold. By treating ECs with 10 ng/ml of TNF-α to induce the expression of adhesion molecules, both types of RBCs showed significant increase in adhesion with higher values in sickle RBCs.

After confirming the adhesion-promoting effect of TNF-α on RBCs adhesion, experiments were conducted to determine the effects of treatment compounds on RBCs-ECs adhesion. Using a t-test, FIG. 5 shows that PSI-14 treatment significantly decreased the adhesion of normal RBCs by more than 75% when compared to TNF-α only (positive control). PSI-13, LMWH, and SNACH also decreased the adhesion by 20-35%. The error bars show the standard deviations of the mean adherence values.

When using sickle RBCs, the addition of PSI-14 or SNACH significantly decreased the adhesion of sickle RBCs when compared to TNF-α only (positive control). In contrast, the LMWH tinzaparin did not show a decrease in the adhesion that could be considered statistically significant (P=0.08). Statistical analysis by one-way ANOVA showed the same significant results for P-Selectin inhibitor (PSI-14) and SNACH with P-value <0.01 (FIG. 6).

In an animal study in sickle cell transgenic mice, the anti-adhesive effects of treatment compounds in the transgenic sickle mouse model were evaluated by measuring ICAM-1 and P-selectin levels in mice plasma.

Compared with healthy wild mice, the plasma of transgenic sickle mice showed significantly higher levels of ICAM-1 (FIG. 7: P=0.02). Using One-way ANOVA calculations validated the significance of the results with a P value <0.05.

For transgenic sickle mice that were treated with LMWH, levels of ICAM-1 at multiple time points showed a decrease only on the first and third days of treatment, and the results were statistically significant (FIG. 8). SCD mice treated with LMWH showed higher mortality rate (3 mice died=75% of the group's mice) than those injected with SNACH or PSI-14 because of bleeding complications. Using One-way ANOVA analysis validated the significance of the results with P value <0.05.

Treatment of transgenic sickle mice with SNACH, levels of ICAM-1 at multiple time points showed a linear decrease over time of treatment. The results were statistically significant for all days of treatment (FIG. 9).

For transgenic sickle mice that were treated with PSI-14, levels of ICAM-1 at multiple time points did not show any decrease over time of treatment, and the results were statistically insignificant (FIG. 10).

Compared with healthy wild mice, the plasma of transgenic sickle mice used in this study significantly showed more than 50% higher levels of P-selectin (FIG. 11: P=0.004). Using One-way ANOVA analysis validated the significance of the results with P value <0.05.

For transgenic sickle mice that were treated with LMWH, levels of P-selectin in multiple time points showed a decrease by almost 15%, and the results were statistically significant only in the first day of treatment (FIG. 12).

For transgenic sickle mice that were treated with SNACH, levels of P-selectin in multiple time points showed a linear decrease over time of treatment down by almost 25%. The results were statistically significant only on day 7 of treatment with P=0.004 (FIG. 13). Using One-way ANOVA calculations validated the significance of the results with P<0.05.

For transgenic sickle mice that were treated with PSI-14, levels of P-selectin in multiple time points showed a decrease over time of treatment, and the results were statistically significant only at the first day of treatment (FIG. 14).

In vitro RBCs adhesion assay were used in the first part of the study. One of the major advantages of the assay developed in conjunction with the present invention is the use of non-radioactive dye (PKH67) to label RBCs. Researchers in the last couple of years tend to use sodium chromate ($^{51}Cr$); a radioactive label to conduct static and dynamic RBCs' adhesion studies. Results of this assay showed higher adhesion of sickle RBCs to endothelium compared to normal RBCs, which showed very little binding. Moreover, the addition of TNF-α to increase the expression of adhesion molecules brought the adhesion of RBCs to even higher levels, and this is what happens in SCD where there are elevated levels of inflammatory biomarkers including TNF-α. These results can be explained by the abnormal nature of sickle RBCs adhesion to the endothelium, and the fact that sickle cells' adhesion increases the activity of the NFκB, which further upregulates the expression and activity of adhesion molecules like ICAM-1 and VCAM-1. The studies conducted for the present invention showed significant inhibitory effect of SNACH and its nanoformulation on normal and sickle RBCs adhesion. These results are consistent with these compounds having the ability to inhibit the interaction of RBCs and endothelial layer of blood vessels.

On the basis of these results, the effect of these compounds on the levels of ICAM-1 and P-selectin in mice plasma were studied, which were significantly higher in transgenic mice than wild ones in the basal state. LMWH and SNACH treatments were capable of lowering both ICAM-1 and P-selectin levels.

In conclusion, using in vitro adhesion assay and SCD mouse model data showed that LMWH, SNACH, and their nanoformulations were able variably to inhibit the adhesion of sickle RBCs to endothelial cells.

Heparin exhibits anticoagulation activity, which makes Heparin a very suitable choice in targeted therapy of the sickle cell-antagonizing hyper-coaguable state of the disease. Interestingly, heparin affects every aspect of SCD pathogenesis including inhibition of inflammation and abnormal cell adhesion in addition to increasing NO synthesis.

In this application, the potential effects of novel GAGs treatment namely SNACH, and their Nanoformulations versus P-Selectin inhibitor or the known Low Molecular Weight Heparin Tinzaparin in sickle cell models were determined.

Inflammation plays a major in various vascular disorders such as atherosclerosis, sickle cell, and associated organ dysfunction such as lung injury. The impact of SNACH on acute inflammatory stimulation was determined using LPS in mice model. FIG. 15 shows the protocol for the study where LPS was administered in a group of mice and in another group SNACH was administered followed by LPS. SNACH effectively suppressed LPS-mediated elevation in blood levels of IL-1 beat (FIG. 16) and Eotaxin (FIG. 17).

The impact on SNACH on various vascular disorders (including atherosclerosis, Sickle cell, Scleroderma and associated organ complications such as lung injury) was determined.

FIG. 18 shows that SNACH at steady laminar flow (s-flow) increased ERK5 transcriptional activity, and crucial role of SR-BI in regulating s-flow and SNACH-induced ERK5 transcriptional activity and down-regulation of inflammatory genes and up-regulation of anti-inflammatory genes expression were shown (FIG. 18: a, b). RAW264.7 cells (a) and HUVECs (b) were transfected with plasmids encoding Gal4-ERK5 and the Gal4-responsive luciferase reporter pG5-Luc. Eighteen hours post transfection; cells were treated with either SNACH or vehicle at final concentration as indicated. With respect to FIG. 18: c, HUVECs were transfected with SR-BI siRNA or GC control, and ERK5 transcriptional activity was assayed. With respect to FIG. 18: d, HUVECs were transfected by control or SR-BI siRNA for 24 hours then cells were treated by SNACH (1 or 2 µg/ml as indicated) for 16 hrs.), and qRT-PCR was used to detect expression of inflammation-related genes as well as IL-10, eNOS, and KLF2 (FIG. 18: d).

Furthermore, SNACH increased C1qc and Mfg-e8 via ERK5. Peritoneal macrophages isolated from NLC or ERK5-MKO mice were treated with SNACH at 1 mg/ml for 18 hours and qRT-PCR was used to detect expression of indicated opsonins and ERK5 (FIG. 19).

With respect to leukocyte adhesion in carotid artery after partial ligation of the left carotid artery (LCA), FIG. 20 shows that three of four caudal branches of LCA in ApoE-/- mice were ligated. Three days after ligation, leukocyte adhesion was detected in LCA as a d-flow model, and the right carotid artery (RCA) as a steady laminar flow model. RCA was dilated more than LCA cells stayed over 1 min.

SNACH demonstrated effective suppression of inflammatory cells accumulation in antigen-induced lung injury (FIG. 21).

FIG. 22 depicts an effect of SNACH on airway hypersensitivity to Methacholine: SNACH group reacted in a pattern similar to that of the unchallenged group.

FIG. 23 depicts an effect of SNACH on OVA-mediated Collagen Lung tissues increase. Lung tissues were hydrolyzed and then hydroxyproline was measured using a colorimetric assay. SNACH blocks collagen synthesis or accumulation.

Example 1

(a) Preparation of Sulfated Non-Anticoagulant LMWH (SNACH)

Preparation of non-anticoagulant LMW heparin (NACH): Heparin was fragmented by periodate oxidation based on a procedure from Islam et al., (Carbohydrate Research 337 (2002) 2239-2243). Briefly, heparin, sodium salt (20 g, 1.43 mmol) was dissolved in 175 mL of distilled water. The pH was adjusted to 5.0 using 1 M HCl. NaIO4 (15 g, 0.07 mol), dissolved in 500 ml, water, was added in a single portion with stirring. The pH was readjusted to 5.0 using 1 M HCl and left for 24 h at 4° C. in the dark. The solution was dialyzed against 4 volumes of water (with one change of water) for 15 h at 4° C. To the approximately 1.5 L of solution obtained after dialysis, 32 mL of 10 M NaOH was added. The solution was stirred at room temperature for 3 h. To prevent the development of colored products, this step was done in the dark. NaBH4 (1 g, 0.026 mol) was added in one portion, and the approximately 1.5 L of solution was stirred for 4 h. The pH was then adjusted to 4.0 using 37% HCl, and the solution was stirred for an additional 15 min. The solution was neutralized to pH 7.0 using 1 M NaOH and NaCl (32.8 g, 0.56 mol) followed by the addition of 2.54 L ethanol. The solution was left for 3 h without stirring, and the precipitate was recovered by centrifugation (22,000×g) for 20 min. The precipitate, recovered by decantation, was suspended in 400 mL absolute ethanol. The solution was filtered using a Buchner funnel, and the recovered solids were left to dry for 5 h under vacuum affording 14.2 g of product. The product was dissolved in 190 mL of water. NaCl (2.8 g, 0.05 mol) was added, and the pH was adjusted to 3.5 using 1 M HCl. The volume was adjusted to 280 mL using water. Absolute ethanol (240 mL) was added with stirring. The solution was stirred 15 min and then left without stirring for 10 h at room temperature. After decanting, the precipitate was recovered and dissolved in water. The ethanol was removed by rotary evaporation under reduced pressure, and the residue was freeze dried affording 10 g of NACH.

(b) Size Fractionation of Non-Anticoagulant LMW Heparin (NACH)

The parent porcine mucosal heparin has an average molecular weight ~12 000, while the resulting heparin fragments have an average degree of polymerization (dp) of 16, corresponding to a low molecular weight heparin of average molecular weight ~5000 (range from dp8 to dp24). To do the size fractionation in a 100 mg scale, the LMW NACH (200 mg/mL in 0.2 M sodium chloride, pH 7.0) is loaded onto a Bio-Gel P-6 column (i.d. 2.6/96 cm), eluted with 200 mM sodium chloride, and fractions (3 mL each) are collected at a flow rate of 16 mL/h. Fractions corresponding to each prominent peak with average MW of 6,000 Da and 4,000 Da are pooled based on total carbohydrate analysis and PAGE analysis. The volume was reduced to about 10 mL using a rotary evaporator. The final products were desalted with dialysis tube (MWCO 1000) and lyophilized.

(c) Preparation of NACH with Different Sulfation Levels

Three sulfation levels (low, middle, and high) of LMW NACH will be prepared with Vivapure Q Maxi H spin columns (Sartoriou Stedim Biotech, Bohemia, N.Y.). 20 mg of LMWH or LMW NACH is loaded onto a Vivapure Q Maxi H spin column and eluted step wisely with 10 mL of 200 mM, 800 mM and 2000 mM sodium chloride and fractions are collected separately. Fractions eluted from 200 mM, 800 mM and 2000 mM sodium chloride are corresponding to the three sulfation levels Sulfate/Carboxylate ratio [low (1.5-2.4/1) for NACH, middle (2.4-3.5/1) for SNACH, and high (3.5-5/1) for S-SNACH]. Alternatively, chemical or enzymatic sulfation were carried out for controlled sulfation. The final products were desalted with dialysis tube and lyophilized.

Example 2

Synthesis of Chitosan (CS) Poly L-Arginine (PLAR) Conjugate (CS-PLAR)

The Chitosan poly L-arginine (CS-PLAR) conjugates are synthesized where the conjugation is achieved by amide bond linkage between the amine group (—NH2) of CS and the carboxyl group (—COOH) of PLAR (FIG. 1). Briefly, for conjugation of CS and PLAR, 5 ml of CS solution (1 mg/ml) is mixed with 5 ml of PLAR (1 mg/ml) and then added to 800 mg of 1-ethyl-3-(3-dimethylaminopropyl) carbodiimide hydrochloride (EDC) and 1 gram of N-hydroxysulfosuccinimide (Sulfo-NHS). After 24 hours, the resulting CS-PLAR conjugates are separated by membrane-filter. Further dialysis will be performed for purification. The final solution is lyophilized for further studies. The number of L-arginine used ranged from 10-100 repeated units (FIG. 2).

Example 3

Synthesis of Chitosan-Poly L-Arginine Nanoparticles (CS-PLAR-NPs)

A Chitosan-Poly L-arginine nanoparticle (CS-PLAR-NPs) is synthesized in mild acidic conditions by promoting the interaction of the $NH_3$ group present in chitosan with the phosphate group present in tripolyphosphate (TPP). Briefly, to 10 ml of a solution 1% CS-PAR conjugate, 1 ml of a triphosphate disodium salt (1 mg/ml in deionized water) is added drop by drop, with constant stirring. The entire solution is then sonicated for about 30 seconds using a probe sonicator, and allowed to stir for another 4 hours. This solution is lyophilized to get the nanoformulation in powdered form. The lyophilized powder will be re-dispersed in phosphate buffered for further use.

Example 4

Synthesis of Poly L-Arginine—PLGA or Hyaluronic Acid (HA) and their Nanoparticles The same protocol used as in examples 2-3 for the conjugation of Poly L-arginine with PLGA or HA conjugation through the $NH_2$ of the poly L-arginine and COOH group of PLGA or HA.

Example 5

Synthesis of Poly L-Arginine Nanoparticles Having GAGs Ionically Complexed Along with Site Directed Delivery to Vascular Tissues Conjugation of ligand to a targeted moiety such as the integrin alpha v beta 3 such as cyclic N-Methyl-Arginine-Glycine-Aspartic acid (N-ME-Arg-Gly-Asp), and other known high affinity ligands to alpha v integrin. The Poly L-arginine may also or alternatively cross-linked to the targeted moiety of P-selectin inhibitor (PKI). Generally, the targeted moiety is conjugated to the shell of the nanoparticle to effectuate a targeted delivery of the nanoparticle to a specified target in a subject such as a human being or mammal.

Example 6

Synthesis of Poly L-Arginine Nanoparticles Having GAGs Ionically Complexed Along with Site Directed Delivery to Vascular Tissues Conjugation of ligand to the Receptors for Glycosylated End products (RAGE) differentially expressed in pulmonary tissues such as RAGE aptamer, and other known high affinity ligands to RAGE.

Example 7

Materials

Gelatin (G-1393) and PKH-67 label (MIDI67) were purchased from Sigma-Aldrich (St. Louis, Mo.). HUVEC(CC-2519), EGM complete media (CC-3024), trypsin/EDTA (CC-5012), trypsin neutralizing solution (TNS-CC-5002), and HEPES buffered saline solution (CC-5022) were obtained from Lonza (Allendale, N.J.). Tissue culture supplies including flasks and well plates were obtained from Celltreat® (Shirley, Mass.).

Example 8

Cell Culture

Using gelatin-coated culture flasks, HUVEC were cultured in EGM complete media supplemented with 2 ml bovine brain extract (BBE), and passaged when 80% confluent using trypsin/EDTA solution according to the manufacturers' instructions. Cells from passages 2 to 6 were used for adhesion assay experiments. Cells were sub-cultured in a 96-well plate pre-coated with collagen with a number of 20,000 cells per well, and were left for 24 hours at 37° C. in a $CO_2$ (5%) incubator to form a confluent monolayer.

Example 9

Packed RBCs Separation

Normal and sickle blood samples were collected in EDTA tubes from the antecubital vein of healthy volunteers and homozygous sickle cell patients, respectively. RBCs were separated from whole blood by centrifugation (1000×g for 10 minutes), and plasma was collected and stored at −80° C. Packed RBCs were washed once with PBS, and counted using a CBC analyzer. Then $50 \times 10^6$ single red blood cells were transferred into a 15 ml conical tube, and re-suspend into 5 ml PBS. Finally cells were centrifuged at 1000×g for 10 minutes to yield a loose pellet.

Example 10

PKH67 Labeling of RBCs

Normal and sickle RBCs were labeled using the PKH67 green fluorescent cell linker kit according to the manufacturer's instructions. Briefly, 50 µl ($50 \times 10^6$ cells) of single red blood cells were incubated with 4 µl PKH67 dye in 2 ml diluent C for 5 min at room temperature with periodic mixing. The staining was stopped by adding 2 ml of 1% BSA for 1 minute and the cells centrifuged at 1000×g for 10 minutes. The supernatant was removed, and the packed RBC pellet was washed 4 times by centrifugation in complete medium to ensure removal of unbound dye. After the final wash, the packed RBC pellet was resuspended in complete medium to yield a final concentration of $1 \times 10^7$ cells/ml.

Example 11

Static Adhesion Assay

After HUVECs formed a confluent monolayer in the plate's wells, the experiment was designed to include five groups in centuplicate: medium only (negative control), TNF-α only (positive control), or TNF-α with the treatment compounds: LMWH, SNACH, and PSI. All ECs except the negative control group were treated with TNF-α (10 ng/ml) for 1 hour to increase the expression of adhesion molecules like ICAM, VCAM, P- and E-selectin on the ECs' surface. HUVECs were rinsed with PBS and 200 µl of media were added to each well. Both HUVECs and labeled RBCs were incubated with treatment compounds (PSI 10 µg/ml, LMWH & SNACH 40 µg/ml) for 45 min at 37° C. The media were removed from the plate's wells and 200 µl of labeled RBCs ($2 \times 10^6$ cells) were added to each well and incubated at 37° C. for 45 minutes. Non-adherent RBCs were removed with PBS wash, and then 150 µl of complete medium were added for plate reading.

Example 12

Standard Curves of PKH67-Labeled RBCs

In order to quantitate endothelial-adherent RBCs by the fluorescence plate reader, serial two-fold dilutions of PKH67-labeled RBC samples were prepared from $2 \times 10^6$ to $0.16 \times 10^6$ RBCs/well. PKH26 fluorescence was detectable with as few as $10^4$ RBCs.

Example 13

Measurements of Adherent RBCs

Plates were read in a fluorescence mode using BioTek® micro-plate reader (Winooski, Vt.) at an excitation 485 nm and emission 528 nm. The number of bound PKH67-labeled RBCs in each sample was calculated from the corresponding standard RBC curve using Excel software.

TABLE 1

Effect of Inhibitors of SNACH Nanoformulation on Sickle RBC-EC Adhesion

| Compounds | Mean % Inhibition of Sickle RBC-EC Adhesion ± SEM |
|---|---|
| A-SNACH | 45 ± 5 |
| B-SNACH Poly L-Arginine | 95 ± 3 |
| C-SNACH Poly L-Arginine/Chitosan | 90 ± 5 |

Data represent average % inhibition of RBC adhesion to endothelial cells. All compounds listed were tested at 1.0 uM SNACH.

Example 14

Sickle Transgenic and Wild Mice

Transgenic SCD model mice (stock #013071) of aged-matched female were obtained from The Jackson Laboratory (Bar Harbor, Me.) in addition to wild mice as controls. Genetically, transgenic mice were designed with the human hemoglobin gamma ($^A\gamma$) gene and the human sickle hemoglobin beta ($\beta^S$) gene replacing the endogenous mouse major and minor β-globin.

Example 15

Injection of Compounds and Blood Collection

Each category of mice (wild or SCD) was divided into three groups. Basal blood samples were taken by retro orbital venipuncture under anesthesia with citrated micro-hematocrit tubes, before the treatment administration. The three groups in each category were treated subcutaneously with LMWH (5 mg/kg), SNACH (20 mg/kg), and PSI (10 mg/kg). Compounds were administered daily for 7 days, and follow up blood samples were drawn daily after 1 hour of treatment administration. Immediately after collection, blood was centrifuged at 800×g for 5 minutes and plasma was collected and stored at −80° C.

Example 16

Measurement of Blood Biomarkers

Levels of adhesion biomarker ICAM-1 were measured in mice plasma using the Bio-Plex 200 systems. Assay kit (171-304080M) was obtained from Bio-Rad (Hercules, Calif.) and the experiment was conducted following the provided instructions. The assay principle is based on the concept of sandwich ELISA where magnetic beads are covalently bound to the capture antibodies that react to the targeted biomarker. Additionally, second detection antibodies with streptavidin-phycoerythrin (SA-PE) conjugate complete the sandwich complex.

Example 17

Effect of SNACH on Endothelial TFPI

The tests used primary cell line: Human Umbilical Vein Endothelial Cells (HVEC) passage 2 and grown for 4 days. Cells plated on Day 4, removed EBM, add serum free medium (RPMI), and incubated for 2 hours prior to the addition of SNACH at different concentrations. Cell media were collected at baseline, 0.5, 1, 2, 4, and 24 hours. Standard ELISA method was used for TFPI measurements (Table 2).

TABLE 2

Effect of SNACH on human Endothelial TFPI release over time

| Time Post-SNACH (Hours) | TFPI (Pg./ml) above baseline |
|---|---|
| 0.5 | 15 |
| 1.0 | 36 |
| 2.0 | 39 |
| 4.0 | 25 |

Example 18

Effect of SNACH Versus the LMWH Tinzaparin on aPTT

To 0.1 ml of citrated plasma 0.1 ml of human placenta lipid is added and the mixture is incubated for 2 min at 37° C. The coagulation process is initiated by the addition of 0.1 ml 25 mM calcium chloride and the time to clot formation is determined. The aPTT measures effects on the endogenous pathway of coagulation.

Neither SNACH nor its Nanoformulations (Poly L-Arginine or Poly L-Arginine cross bridged with Chitosan, PLGA or Hyaluronic acid) have any effect on aPTT at SNACH 1-10 uM. In contrast, LMWH such as tinzaparin or S-LMWH resulted in a concentration dependent increase in aPTT.

Example 19

Effect on Platelet/Fibrin Clot Dynamics in the Presences of Cup Coated with Endothelial Cells Thrombelastography (TEG) was performed in either citrated whole blood after re-calcification. The blood samples were mixed with 3.8% tri-sodium citrate solution (one part citrate solution to 9 parts blood) as anticoagulant. The citrated whole blood was re-calcified by adding 0.4 ml isotonic calcium chloride solution. An aliquot of 0.36 ml of the re-calcified whole blood was transferred to the pre-warmed cup (Coated with monolayer of HUVEC or not) of the thrombelastograph. The following measurements were the standard variables of TEG: (i) Reaction time (R): the time from sample placement in the cup until onset of clotting (defined as amplitude of 1 mm). This represents the rate of initial fibrin formation; (ii) Maximum amplitude (MA): greatest amplitude on the TEG trace, wherein MA represents the absolute strength of the fibrin clot and is a direct function of the maximum dynamic strength of fibrin and platelets. SNACH and its different types of Poly L-Arginine Nanoparticles did not affect platelet/fibrin clot dynamics in the absence of endothelial cell coating. SNACH and its Nanoformulations significantly suppressed platelet/fibrin clot dynamics only in the presence of endothelial cell coating, which was reversed by anti-TFPI. In contrast, the LMWH tinzaparin or sulfated LMWH resulted in suppression of platelet/fibrin clot dynamics either in the presence or absence of cup coated with endothelial cells.

Example 20

Effect of SNACH Versus the LMWH Tinzaparin on Bleeding Time in Mice

Mice dosed with SNACH alone or Nanoformulated with the various forms of Poly L-Arginine NPs at doses ranging from 0.1-40 mg/Kg, Subcutaneously did not result in any effect on bleeding time, anti-Xa or aPTT. In contrast, the LMWH tinzaparin at doses ranging from 0.1-5.0 mg/Kg, Subcutaneously resulted in maximal increase in bleeding time with browsing at site of injection, inhibition of factor Xa and increase in aPTT.

Example 21

Effect of NFkB

The Luciferase Assay System was purchased from Promega (Madison, Wis., USA). NF-KB Luciferase Reporter Hela Stable cells were seeded at $10^4$ cells/well in 96-well plate and incubated for 24 hours. Then, growth media was removed. Next, SNACH, tinzaparin or Poly-Arginine NPs were added at concentrations of 1 μL, 10 μL and 100 μL in triplicate and incubated at 36° C. for two hours. After two hours, cells were washed with PBS. Lysis buffer was prepared following a generic protocol. 0.5 mL of lysis buffer was mixed with 2 mL of PBS. Next, the lysis buffer's solution was added to each well. Afterward, the 96-well plate was rocked several times using a shaker. Cells and liquid were collected for centrifugation at 1200×g for 5 minutes at 4° C. The supernatant was removed and stored at −80° C. One week later, the 96-well plate was placed in the luminometer containing 20 μL of lysis buffer and 100 μL of luciferase assay reagent/well. The light was measured for a period of 10 seconds with a delay time of 2 seconds.

SNACH, tinzaparin or their Poly-Arginine Nanoformulations resulted in a significant concentration-dependent suppression of NFkB activation.

Example 22

SNACH and Anti-Inflammatory Effects Against Endotoxin (LPS)-Mediated Elevation of Pro-Inflammatory Stimuli in Mice LPS was administered to mice at 0.01 mg/Kg, IP and in another group of mice LPS was injected followed by SNACH at 5.0 mg/Kg, SC. Blood samples were withdrawn at different interval for the measurement of blood levels of various chemokines and cytokines using bioplex. LPS raised the blood levels of various cytokines and chemokines SNACH treatment suppressed the LPS-mediated elevation of chemokines and cytokines (FIGS. 16, 17).

Example 23

SNACH and Atherosclerosis: Endothelial Lipase (EL) Atherosclerosis

EL is one of several lipases secreted by human macrophages, and its expression in macrophages has been observed in human atherosclerotic lesions. Several clinical studies suggest that EL could be implicated in atherosclerosis For example; an increased level of plasma EL has been associated with visceral obesity, metabolic syndrome, inflammation, and premature coronary heart disease.

Example 24

SNACH and Atherosclerosis Mechanisms

LMWH and heparin impact on hemostasis and possess bleeding adverse effect that limit their long-term use. Hence, the present invention developed a novel Sulfated Non-Anticoagulant LMWH (SNACH) that maintain all pharmacological actions of LMWH including endothelial release of Tissue Factor Pathway Inhibitor (TFPI) but is devoid of anti-thrombin (ATIII) binding to affect circulating coagulation factors such as factor Xa, factor IIa, and other ATIII-dependent coagulation factors.

One of the possible targets for SNACH is TFPI, which is expressed in many cells relevant to atherosclerosis including platelets, endothelial cells, vascular smooth muscle cells, and monocyte/macrophages. In human carotid plaques, the level of TFPI expression is inversely associated with TF activity, suggesting a local regulatory role. In plasma, TFPI exists in small quantities (<5%) as a free full-length protein but is predominantly associated with lipoproteins. Vascular overexpression of TFPI has been shown to reduce acute thrombosis and neointimal formation following vascular injury in murine models. Similarly, TFPI haplo-insufficiency increases the atherosclerotic burden and thrombotic tendency in wild-type and apoE-deficient backgrounds. Taken together, these findings suggest a potentially important role for TFPI in the development and progression of acute and chronic vascular disease. SNACH is effective in releasing endothelial TFPI and increase plasma TFPI level in mice.

Example 25

SNACH and Atherosclerosis Mechanisms (a) SNACH and Anti-Inflammatory Mechanisms:

The crucial role of extracellular signal-regulated kinase 5 (ERK5) in regulating both ECs and M is inflammation have been reported. ERK5, an atypical mitogen activated protein kinase with transcriptional activity, has not only a kinase domain but also a transcriptional activity domain, the latter being regulated by an intra-molecular interaction independent of its kinase activity. ERK5-KLF2 signaling is involved in the laminar-flow-induced eNOS expression and anti-inflammatory effects. These results collectively suggest that activating ERK5 is a novel approach to protecting ECs.

Therefore, the present invention first investigated whether SNACH can increase ERK5 transcriptional activation, and subsequent anti-inflammatory gene in ECs and opsonins in MΦs, and indeed found that these events were up-regulated by SNACH treatment in both ECs and MΦs (FIGS. 18 and 19). The present invention also found that SNACH treatment increased TFPI secretion and its plasma level in vivo. Interestingly, the present invention also found the involvement of SR-B1 in SNACH induced anti-inflammatory gene expression and opsonins induction in vitro (FIGS. 18 and 19).

(b) Generation of ERK5$^{fl/fl}$ LysMCre$^{+/-}$ (ERK5-MKO) Mice:

Genetic deletion of ERK5 in mice leads to an embryonic-lethal phenotype[58]. ERK5$^{fl/fl}$ C57bl/6 mice were crossed with those expressing Cre under the lysozyme M (LysM) promoter to generate ERK5$^{fl/fl}$ LysM-Cre$^{+/-}$ (ERK5-MKO) mice. The LysM locus in mice is exclusively active in hematopoietic cells of the myelomonocytic lineage, being expressed highly in mature MΦs and neutrophils. ERK5 expression was markedly diminished in peritoneal M is from ERK5-MKO mice. Up to 6 months of age, there was no observation of any differences in size or body weight between ERK5-MKO and non-transgenic littermate control (NLC) mice, and no notable differences were found in their life span, gross anatomy or complete blood counts. Since ERK5 regulates efferocytosis, the present invention investigated expression of opsonins and their receptors in MΦs. The present invention found that expression of opsonins such as MerTK, C1qa, C1qb, C1qc, Gas6, Mfge8, Thbs1, and Anxa1 was ~40-80% lower in ERK5-MKO MΦ. In agreement, immunoblot analyses revealed a ~200% decrease in Thbs1 and Mfge8 in ERK5-MKO MΦ. The mRNA expression of receptors for "Find-me" (LPC) and "Eat-me" (Tim 4) was increased upon AC feeding in MΦs from NLC mice, whereas their expression was significantly lower in AC-fed ERK5-MKO MΦ. In contrast, "Don't eat-me" (CD47) expression was decreased in NLC MΦs by ACs ingestion, but a significantly higher level of expression was noted in ERK5-MKO MΦs with and without AC administration. In addition, constitutive activation of ERK5 by CA-MEK5 increased opsonin mRNA expressions. These data show that ERK5 activation increases efferocytosis-related molecule expression.

(c) SNACH Increased ERK5 Activity in MΦs, and C1qc and Mfge8 Expression in PE MΦs.

Whether SNACH can increase ERK5 phosphorylation and ERK5 transcriptional activity in PE MΦs was examined, and it was found that SNACH significantly increased both of them [data not shown and FIG. 18a]. Furthermore, the present invention found that SNACH also increased opsonins of C1qc and Mfge8 expression via ERK5 [FIG. 19]. These data suggest the possible role of SNACH in regulating efferocytosis and subsequent AS formation.

(d) SNACH Increased ERK5 Transcriptional Activity as Well as Anti-Inflammatory Gene Expression and Decreased Inflammatory Gene Via SR-BI in ECs.

It was also found that SNACH increased ERK5 transcriptional activity [FIG. 18b]. One of the possible targets of SNACH is endothelial lipase (EL), which has conserved heparin-binding properties and lipid binding domains and expresses in both ECs and MΦ. EL can promote the remodeling and elimination of HDL particles via scavenger receptor class B type I (SR-BI). In addition, the essential role of EL activity in HDL-induced adhesion molecule inhibition through PPARα activation in ECs has been reported. As shown in FIGS. 18c and 18d, the present invention found the crucial role of SR-BI in regulating steady laminar flow-induced ERK5 transcriptional activity, which subsequently increases PPARs activation. Therefore, the role of SR-BI in SNACH-mediated anti- and pro-inflammatory gene expression was investigated. As shown in FIG. 18e, SNACH treatment significantly inhibited basal level of pro-inflammatory gene expression (adhesion molecules and MCP-1). In contrast, SNACH increased anti-inflammatory gene expression (IL-10, eNOS, and KLF2). The depletion of SR-BI by siRNA in ECs did not change or slightly increased pro- and anti-inflammatory gene expression (FIG. 18e). Interestingly, SNACH treatment did not inhibit but instead significantly increase pro-inflammatory gene expression, and lost its induction properties against anti-inflammatory gene expression under SR-BI depletion (FIG. 18e). These data suggest that the anti-inflammatory effect of SNACH in ECs is SR-BI dependent. Since both pro- and anti-atherogenic effects of EL have been reported[2], the induction of pro-inflammatory gene expression by SNACH under SR-BI depletion may explain its complexity.

Example 26

SNACH and Leukocyte Adhesion: EC-Specific ERK5 Depletion Induces AS

Because systemic knockout of ERK5 is embryonic lethal for mice, tamoxifen (4-OHT: -hydroxytamoxifen)-inducible EC-specific ERK5 KO mice were generated by crossing mice expressing tamoxifen-inducible Cre-recombinase Cre-ER$^{T2}$ under the regulation of the vascular endothelial cadherin (VE-cad) promoter[74] with a conditional KO line of ERK5. To induce deletion of the Erk5 gene, heterozygous VE-Cad-CreER$^{T2}$/Erk5$^{flox/-}$ (Inducible ERK5-EKO+/−) mice were injected with peanut oil or 2 mg of 4-OHT for 5 times daily. Reduced endothelial ERK5 expression in these mice was confirmed by Western blotting using lung ECs isolated by anti-PECAM-1 conjugated magnetic beads. To examine the role of ERK5 on atherogenesis, the inducible ERK5-EKO+/− mice was crossed with LDLR−/− mice. When these mice were fed with a high-fat diet for 16 weeks, ERK5-EKO mice compared to VeCad-Cre-LDLR−/− control mice showed increased atherogenesis, suggesting that ERK5 activity was necessary to inhibit AS formation.

Example 27

Ovalbumin Antigen (OVA) Challenge Mediated Lung Injury

Mice were divided into three groups (n=6) and were sensitized with 20 µg ovalbumin adsorbed in 100 µg/ml of Imject Alum by i.p. injection on days 0, 7, 14 (general sensitization) in all mice. On day 14, mice are anesthetized and 100 µg of OVA in 50 µl of PBS administered intranasally in all mice except negative control sensitized with PBS. Mice are again anesthetized before being challenged with 50 µg of OVA in 50 µA of PBS on each day. SNACH at 10 mg/kg were given by i.p. injection 1 h prior to OVA administration.

Example 28

Airway Hyper-responsiveness: Mice were subjected to Methacholine (MeCh) exposure at 2 weeks and 4 weeks after exposure to Ovalbumin.

Example 29

OVA-mediated Collagen Lung tissues increase: Lung tissues were hydrolyzed and then hydroxyproline was measured using a colorimetric assay. SNACH blocks collagen synthesis or accumulation indicating its potent anti-fibrotic activity (FIG. 23).

The present invention provides a composition, comprising: a nanoparticle. The nanoparticle comprises a shell which encapsulates sulfated non-anticoagulant heparin (SNACH). The shell comprises poly L-arginine. The SNACH is ionically or covalently bonded to the poly L-arginine.

In one embodiment, the SNACH is ionically bonded to the poly L-arginine.

In one embodiment, the SNACH is covalently bonded to the poly L-arginine.

In one embodiment, the poly L-arginine is covalently cross-linked to chitosan, Poly lactic-co-glycolic acid (PLGA), hyaluronic acid, or combinations thereof.

In one embodiment, the poly L-arginine is covalently cross-linked to chitosan. In one embodiment, the poly L-arginine is covalently cross-linked to chitosan by amide bond linkage between an amine group of the chitosan and a carboxyl group of the poly L-arginine.

In one embodiment, the shell encapsulates a P-selectin inhibitor (PSI).

In one embodiment, a targeted moiety is conjugated to the shell of the nanoparticle to effectuate a targeted delivery of the nanoparticle. In one embodiment, the targeted moiety is an integrin avb3 ligand or a P-selectin inhibitor (PSI).

The present invention provides a method for treating a disorder of a subject, said method comprising: administering to the subject a therapeutically effective amount of the composition of the present invention for treating the disorder, wherein the disorder comprises a vascular disorder, a complication of the vascular disorder, or a combination thereof.

In one embodiment, the disorder comprises the vascular disorder.

In one embodiment, the vascular disorder comprises sickle cell disease, atherosclerosis, scleroderma, pulmonary hypertension, or combinations thereof.

In one embodiment, the vascular disorder comprises the sickle cell disease.

In one embodiment, the vascular disorder comprises the atherosclerosis.

In one embodiment, the disorder comprises the complication of the vascular disorder.

In one embodiment, the complication of the vascular disorder comprises a dysfunction of an organ of the subject. In one embodiment, the organ of the subject is a lung of the subject, and wherein the dysfunction is an injury of the lung.

In one embodiment, the subject is a human being or a mammal.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A composition, comprising:
   a nanoparticle comprising a shell which encapsulates sulfated non-anticoagulant heparin (SNACH), wherein the shell comprises poly L-arginine, and wherein the SNACH is ionically or covalently bonded to the poly L-arginine.

2. The composition of claim 1, wherein the SNACH is ionically bonded to the poly L-arginine.

3. The composition of claim 1, wherein the SNACH is covalently bonded to the poly L-arginine.

4. The composition of claim 1, wherein the poly L-arginine is covalently cross-linked to chitosan, Poly lactic-co-glycolic acid (PLGA), hyaluronic acid, or combinations thereof.

5. The composition of claim 4, wherein the poly L-arginine is covalently cross-linked to chitosan.

6. The composition of claim 5, wherein the poly L-arginine is covalently cross-linked to chitosan by amide bond linkage between an amine group of the chitosan and a carboxyl group of the poly L-arginine.

7. The composition of claim 1, wherein the shell encapsulates a P-selectin inhibitor (PSI).

8. The composition of claim 1, wherein a targeted moiety is conjugated to the shell of the nanoparticle to effectuate a targeted delivery of the nanoparticle.

9. The composition of claim 8, wherein the targeted moiety is an integrin $\alpha v \beta 3$ ligand.

10. The composition of claim 8, wherein the targeted moiety is a P-selectin inhibitor (PSI).

11. A method for treating a disorder of a subject, said method comprising:
administering to the subject a therapeutically effective amount of the composition of claim 1 for treating the disorder, wherein the disorder comprises a vascular disorder, a complication of the vascular disorder, or a combination thereof.

12. The method of claim 11, wherein the disorder comprises the vascular disorder.

13. The method of claim 12, wherein the vascular disorder comprises sickle cell disease, atherosclerosis, scleroderma, pulmonary hypertension, or combinations thereof.

14. The method of claim 13, wherein the vascular disorder comprises the sickle cell disease.

15. The method of claim 13, wherein the vascular disorder comprises the atherosclerosis.

16. The method of claim 11, wherein the disorder comprises the complication of the vascular disorder.

17. The method of claim 16, wherein the complication of the vascular disorder comprises a dysfunction of an organ of the subject.

18. The method of claim 17, wherein the organ of the subject is a lung of the subject, and wherein the dysfunction is an injury of the lung.

19. The method of claim 11, wherein the subject is a human being.

20. The method of claim 11, wherein the subject is a mammal.

* * * * *